US012807678B2

(12) United States Patent
Sgourakis

(10) Patent No.: US 12,807,678 B2
(45) **Date of Patent: *Nov. 24, 2026**

(54) MHC CLASS I COMPOSITIONS AND METHODS

(71) Applicant: The Regents of the University of California, Oakland, CA (US)

(72) Inventor: Nikolaos G. Sgourakis, Philadelphia, PA (US)

(73) Assignee: THE REGENTS OF THE UNIVERSITY OF CALIFORNIA, Oakland, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 17/141,096

(22) Filed: Jan. 4, 2021

(65) Prior Publication Data

US 2021/0371498 A1 Dec. 2, 2021

Related U.S. Application Data

(60) Provisional application No. 63/076,601, filed on Sep. 10, 2020, provisional application No. 63/011,221, filed on Apr. 16, 2020, provisional application No. 62/957,040, filed on Jan. 3, 2020.

(51) Int. Cl.

| | |
|---|---|
| ***C07K 1/36*** | (2006.01) |
| ***C07K 1/00*** | (2006.01) |
| ***C07K 14/705*** | (2006.01) |
| ***C07K 19/00*** | (2006.01) |
| *C07K 14/74* | (2006.01) |

(52) U.S. Cl.

CPC .......... *C07K 14/70539* (2013.01); *C07K 1/00* (2013.01); *C07K 19/00* (2013.01)

(58) Field of Classification Search

None

See application file for complete search history.

(56) References Cited

U.S. PATENT DOCUMENTS

| | | | | |
|---|---|---|---|---|
| 11,814,420 | B2* | 11/2023 | Sgourakis | B01J 19/0046 |
| 2013/0017213 | A1 | 1/2013 | Liu et al. | |
| 2013/0171668 | A1 | 7/2013 | Loset | |
| 2014/0127251 | A1 | 5/2014 | Maeurer | |
| 2014/0186850 | A1 | 7/2014 | Berniac | |
| 2018/0180601 | A1 | 6/2018 | Pedersen et al. | |
| 2018/0319870 | A1 | 11/2018 | Amin | |
| 2020/0024654 | A1 | 1/2020 | Heron et al. | |
| 2021/0155670 | A1 | 5/2021 | Sgourakis et al. | |
| 2021/0269503 | A1 | 9/2021 | Sgourakis | |
| 2021/0371498 | A1 | 12/2021 | Sgourakis | |
| 2021/0371499 | A1 | 12/2021 | Sgourakis | |
| 2022/0042008 | A1* | 2/2022 | Kleinman | C12N 15/1075 |
| 2023/0059548 | A1* | 2/2023 | Sgourakis | C12N 15/1037 |

FOREIGN PATENT DOCUMENTS

| | | | |
|---|---|---|---|
| EP | 2127664 | A1 | 12/2009 |
| WO | WO 2020/010261 | | 7/2019 |
| WO | WO 2019/145509 | | 8/2019 |
| WO | WO 2021/050792 | | 3/2021 |
| WO | WO 2021/138685 | | 7/2021 |
| WO | WO 2021/138688 | | 7/2021 |
| WO | WO 2021/212085 | | 10/2021 |

OTHER PUBLICATIONS

HLA Nomenclature (2023, 2 pages) (Year: 2023).*
Saini et al (PNAS, Sep. 17, 2013, 110(38): 15383-15388) (Year: 2013).*
Saini et al (PNAS, 2015, 112(1): 202-207) (Year: 2015).*
Hafstrand et al (PNAS, 2019, 116: 5055-5060) (Year: 2019).*
Anjanappa et al (Nature Comm., 2020, 10.1038/s41467-020-14862-4: pp. 1-11) (Year: 2020).*
Ostermeir et al (Mol. Immunol. 2015, 63: 312-319) (Year: 2015).*
Jantz-Naeem and Springer (Curr. Opin. Immunol. 2021, 70: 82-89) (Year: 2021).*
Overall et al (Nature Communications, 2020, doi.org/10.1038/s41467-020-15710-1, pp. 1-13) (Year: 2020).*
Kalergis et al (JM, 2000, 234: 61-70) (Year: 2000).*
International Search Report and Written Opinion for corresponding PCT Application No. PCT/US2019/040616—9 pages (Nov. 18, 2019).
European Search Report for corresponding EP Patent Application No. EP 19831548—2 pages (Apr. 11, 2022).
International Search Report and Written Opinion for related PCT Application No. PCT/US20/50276—23 pages (Mar. 15, 2021).
International Search Report and Written Opinion for related PCT Application No. PCT/US21/12117—17 pages (May 21, 2021).
International Search Report and Written Opinion for related PCT Application No. PCT/US21/27841—15 pages (Oct. 1, 2021).
International Search Report and Written Opinion for related PCT Application No. PCT/US21/12114—17 pages (May 20, 2021).
Dash et al., Nature 547(7661):89-93 (2017).
Stoeckius et al., Nat Methods (9):865-868 (2017).
Takahashi et al., Proc Natl Acad Sci USA 85(9):3105-9 (1998).
Kawakami et al., J Exp Med. 180(1):347-52 (1994).
Natarajan et al., Nat Commun. 8:15260 (2017).
Glanville et al., Nature 547: 94-98 (2017).
Bakker et al., Proc. Natl. Acad. Sci. U. S. A. 105: 3825-3830 (2008).
Saini et al., Proc. Natl. Acad. Sci. U. S. A. 112: 202-207 (2015).
Morozov et al., Proc. Natl. Acad. Sci. U. S. A. 113: E1006-1015 (2016).

(Continued)

*Primary Examiner* — Misook Yu
*Assistant Examiner* — Marianne Dibrino
(74) *Attorney, Agent, or Firm* — Morgan, Lewis & Bockius LLP

(57) ABSTRACT

Compositions are provided that comprise peptide receptive MHC class I complexes (peptide receptive MHC-I complexes) that are formed after treatment with a catalytic amount of chaperone (i.e. a ratio of chaperone to MHC-I of less than 1:1). In particular, these peptide receptive MHC class I complexes can be used to form peptide-MHC class I (pMHC-I) multimers that can be used in high throughput applications such as detection of antigen specific T cells and characterization of T cell profiles in subjects.

12 Claims, 8 Drawing Sheets

Specification includes a Sequence Listing.

(56) References Cited

OTHER PUBLICATIONS

Jiang et al., Science 358: 1064-1068 (2017).
Jiang et al., Science 358: Supplemental Material (2017). pp. 1-27.
McShan et al., Nat. Chem. Biol. 14: 811-820 (2018).
Khan et al., J. Immunol. 164: 6398-6405 (2000).
Garboczi et al., Proc. Natl. Acad. Sci. 89: 3429-3433 (1992).
Johnson et al., J. Immunol. Baltim. Md 1950 177: 6548-6559 (2006).
Hermann et al., J. Immunol 191: 5743-5750 (2013).
Trautman et al., Euro J Immunol. 32: 3181-3190 (2002).
Jurtz et al., J. Immunol. Baltim. Md 1950 199: 3360-3368 (2017).
Li et al., J. Mol. Biol. 283: 179-191 (1998).
Overall et al., bioRxiv, pp. 1-31 (2019).
Jurewicz et al., Analytical Biochemistry, Amsterdam NL, 584: (2019). No page numbers cited.
Hermann et al., ELIFE. vol. 4, (2015). pp. 1-22.
Lumistra et al., Journal of Experimental Medicine. 215:5, 1493-1504 (2018).
Letournour et al., Eur J Immunol. 19(12):2269-74 (1989).
Ohashi et al., Nature 316(6029):606-9 (1985).
Altman et al., Science 274(5284):94-6 (1996).
Thomas & Tampé, Science 358: 1060-1064 (2017). no page numbers.
Neveu et al., International Immunology. vol. 18, No. 7, pp. 1139-1145 (2006).
Praest et al., "New insights into the structure of the MHC class I peptide-loading complex and mechanisms of TAP inhibition by viral immune evasion proteins." Mol. Immunol., Pergamon, GB, 113, pp. 103-114 (2018).
Jurewicz et al., "MHC-I peptide binding activity assessed by exchange after cleavage of peptide covalently linked to β2-microglobulin." Analytical Biochemistry, Amsterdam NL, 584: pp. 1-26 (2019).
Kotsiou et al., "Dimerization of soluble disulfide trap single-chain major histocompatibility complex class I molecules dependent on peptide binding affinity." Antioxidants and Redox Signaling. 15:3, pp. 645-655 (2011).
King et al., "Antibody-peptide-MHC fusion conjugates target non-cognate T cells to kill tumour cells." Cancer Immunol. Immunotherapy 62:6, pp. 1-20 (2013).
Li et al., "Engineering superior DNA vaccines: MHC class I single chain trimers bypass antigen processing and enhance the immune response to low affinity antigens." Vaccine., 28, pp. 1911-1918 (2010).
Hermann et al., "TAPBPR alters MHC class I peptide presentation by functioning as a peptide exchange catalyst." eLIFE. vol. 4, pp. 1-22 (2015).
O'Rourke et al., "Production of soluble pMHC-I molecules in mammalian cells using the molecular chaperone TAPBPR." Protein Engineering Design. 32:12, pp. 525-532 (2019).
Arstila et al., "A direct estimate of the human alphabeta T cell receptor diversity." Science 286: pp. 958-961 (1999).
Moritz et al., "High-throughput peptide-MHC complex generation and kinetic screenings of TCRs with peptide-receptive HLA-A*02:01 molecules." Science Immunology. 4:37, pp. 1-12 (2019).
Saini et al., "Empty peptide-receptive MHC class I molecules for efficient detection of antigen-specific T cells." Science Immunology. 4:37, pp. 1-13 (2019).
Nerli et al., "Structure-Based Modeling of SARS-CoV-2 Peptide/HLA-A02 Antigens." Frontiers in Medical Technology. vol. 2, pp. 1-10 (2020).
Hansen "Preparation of Stable Single-Chain Trimers Engineered with Peptide, [32 Microglobulin, and MHC Heavy Chain" CPI 17.5.1-17.5.17 (2009).
Science Direct—Definitions (Accessed 2024, sciencedirect.com/topics/neuroscience/chaperone#), 9 pgs.

* cited by examiner

B

C

MHC CLASS I COMPOSITIONS AND METHODS

CROSS REFERENCE TO RELATED APPLICATIONS

The present disclosure claims priority to U.S. Provisional Patent Application No. 62/957,040, filed on Jan. 3, 2020, U.S. Provisional Patent Application No. 63/011,221, filed on Apr. 16, 2020, and U.S. Provisional Patent Application No. 63/076,601, filed on Sep. 10, 2020, which are hereby incorporated by reference in their entirety.

STATEMENT OF SUPPORT

This invention was made with government support under Grant Numbers 5R01AI143977 and 5R35GM125034, awarded by the National Institutes of Health. The Government has certain rights in the invention.

REFERENCE TO SEQUENCE LISTING SUBMITTED ELECTRONICALLY

The sequence listing contained in the file named "116550-01-5014-US Updated_ST25.txt", created on Mar. 31, 2023, and having a size of 9,656 bytes, has been submitted electronically herewith via EFS-Web, and the contents of the txt file are hereby incorporated by reference in their entirety.

RELATED APPLICATIONS

This application is related to the application published as International Publication Number WO 2020/010261, which is incorporated by reference herein.

BACKGROUND

Cytotoxic T cell activation occurs when a T cell, via its T cell receptor (TCR), recognizes an antigen peptide-MHC class I complex on an antigen presenting cell. Such TCR/peptide-MHC class I interactions are important, for example, for adaptive immunity against pathogens, for the recognition and elimination of tumor cells, as well as the pathogenesis of particular diseases (e.g., autoimmune diseases).

Antigenic peptide-MHC class I (pMHC-I) multimer complexes are useful for the identification of antigen specific T cells, and antigens that activate such T cells. The identification of antigen specific T cells and corresponding antigens can then be used, for example, for the understanding of disease development, as well as in the development of T-cell based therapies (e.g., cancers), in both preclinical and clinical settings.

High-throughput screening strategies using large arrays of peptide-MHC class I multimers can advantageously allow for the large scale identification of antigen specific T-cells and/or antigens that bind to particular MHC class I. Such high-throughput screens, however, are limited by the ability to produce large collections of peptide-MHC class I multimers. The instability of peptide deficient MHC class I molecules, for example, makes large scale production of peptide-MHC class I multimers using such peptide deficient MHC class I molecules difficult to achieve.

To circumvent the problem of unstable peptide deficient MHC class I molecules, conditional MHC class I ligands are used. See, e.g., Rodenko et al., *Nature Protocols* 1(3): 1120-1132 (2006). Such conditional ligand bound to MHC class I can be cleaved by exposure to UV light, or to increased temperature (See, e.g. Luimstra J J et al, *J Exp. Med,* 215, 1493-1504 (2018)). Upon cleavage and in the presence of a peptide of interest, a net exchange occurs wherein the cleaved conditional ligand dissociates with the MHC class I and the peptide of interest associates with the MHC class I, thereby forming the desired peptide-MHC class I complex. Such conditional ligands, however, also have limitations. Conditional ligands almost always result in some sample aggregation and precipitation during the photolysis/peptide exchange step, due to the unstable nature of the transient peptide deficient MHC. Moreover, using suboptimal peptides can lead to high background levels of exchange. As such, there remains a need for new methods of making peptide-MHC class I complex libraries.

SUMMARY

Compositions are provided that comprise peptide receptive MHC class I complexes (peptide receptive MHC-I complexes) that are formed after treatment with a catalytic amount of chaperone (i.e. a ratio of chaperone to MHC-I of less than 1:1). In particular, these peptide receptive MHC class I complexes can be used to form peptide-MHC class I (pMHC-I) multimers that can be used in high throughput applications such as detection of antigen specific T cells and characterization of T cell profiles in subjects.

In a first aspect, provided herein is a method of making a plurality of peptide receptive MHC class I complexes that can accept a high affinity peptide of interest. The method includes: a) incubating a plurality of MHC class I heavy chains, a plurality of β2-microglobulins and a plurality of placeholder peptides under conditions where the MHC class I heavy chains, the β2-microglobulins and the placeholder peptides form a plurality of placeholder peptide-MHC class I (p*MHC-I) complexes and b) contacting the p*MHC-I complexes with a plurality of dipeptides and a plurality of chaperone molecules, where the chaperone molecules are provided at less than a 1:1 molar ratio of chaperone to p*MHC-I, thereby creating the peptide receptive MHC-I complexes.

In certain embodiments, the MHC class I heavy chain is a human HLA, including, for example, an HLA-A, HLA-B, or HLA-C. The MHC class I heavy chain can be a particular human HLA allele such as HLA-A*02.

In certain embodiments, the MHC class I heavy chain is a human HLA, including, for example, an HLA-A, HLA-B, or HLA-C. The MHC class I heavy chain can be a particular human HLA allele such as HLA-A*02.

In other embodiments, the MHC class I heavy chain is a mouse H-2, including for example an H-2D or an H-2L. The MHC class I heavy chain can be a particular mouse H-2 allele such as an H-2Dd or an H-2Ld. In such embodiments the mouse H-2 includes an amino acid substitution mutation in position M228, such as an M228N, M228Q, M228S, M228T or M228Y mutation.

In other embodiments, the plurality of placeholder peptides include destabilizing placeholder peptides with a Tm value for the MHC class I molecule of below 50° C. In one particular example, if the MHC Class I heavy chain is HLA-A*02:01, then one such placeholder peptide could be gTAX/HLAA* or AcLLFGYPVYV (SEQ ID NO:2).

In other embodiments, the dipeptide can be glycyl-methionine or glycyl-phenylalanine.

In other embodiments, the p*MHC-I complexes are purified and biotinylated prior to the contacting with the dipeptides and chaperones.

In other embodiments, the chaperones include TAPBPR.

In still other embodiments, the molar ratio of p*MHC-I to chaperone is less than 1:2, less than 1:10, less than 1:50, less than 1:100, less than 1:500, or less than 1:1000, including any amount of chaperone that is sufficient to convert at least 95% of the p*MHC-I to peptide receptive MHC-I complexes.

In a second aspect, provided herein is a method of making a plurality of peptide-MHC class I (pMHC-I) complexes that each include an MHC class I heavy chain, an β2-microglobulin, and a peptide of interest. The method includes a) incubating a plurality of MHC class I heavy chains, a plurality of β2-microglobulins and a plurality of placeholder peptides under conditions where the plurality of MHC class I heavy chains, β2-microglobulins and placeholder peptides form a plurality of placeholder peptide-MHC class I (p*MHC-I) complexes; b) b) forming a plurality of peptide receptive MHC-I complexes by contacting the plurality of p*MHC-I complexes with a plurality of dipeptides and chaperones, where the chaperones are provided at a molar ratio of chaperone to p*MHC-I complex of less than 1:1; and c) contacting the plurality of peptide receptive MHC-I complexes with a plurality of peptides of interest, thereby forming the plurality of pMHC-I complexes.

In certain embodiments, the MHC class I heavy chain is a human HLA, including, for example, an HLA-A, HLA-B, or HLA-C and in a more particular example, the MHC class I heavy chain is of a particular human HLA allele such as HLA-A*02.

In other embodiments, the MHC class I heavy chain is a mouse H-2, including for example an H-2D or an H-2L and in a more particular example, the MHC class I heavy chain is of a particular mouse H-2 allele such as an H-2Dd or an H-2Ld. In such embodiments, the mouse H-2 includes an amino acid substitution mutation in position M228, such as an M228N, M228Q, M228S, M228T or M228Y mutation.

In other embodiments, the plurality of placeholder peptides include destabilizing placeholder peptides with a Tm value for the MHC class I molecule of below 50° C. In one particular example, if the MHC Class I heavy chain is HLA-A*02:01, then one such placeholder peptide could be gTAX/HLAA* or AcLLFGYPVYV (SEQ ID NO:2).

In other embodiments, the dipeptide can be glycyl-methionine or glycyl-phenylalanine.

In other embodiments, the p*MHC-I complexes are purified and biotinylated prior to the contacting with the dipeptides and chaperones.

In other embodiments, the chaperones include TAPBPR.

In still other embodiments, the molar ratio of p*MHC-I to chaperone is less than 1:2, less than 1:10, less than 1:50, less than 1:100, less than 1:500, or less than 1:1000, including any amount of chaperone that is sufficient to convert at least 95% of the p*MHC-I to peptide receptive MHC-I complexes.

In other embodiments, all the peptides in the plurality of the peptides of interest have the same sequence.

In other embodiments, at least some or all of the peptides in the plurality of the peptides of interest have different sequences.

In other embodiments, at least some or all of the peptides in the plurality of the peptides of interest are tumor antigen peptides, viral peptides, self-peptides, or bacterially derived peptides.

In a third aspect, provided herein is a method of making a plurality of peptide-MHC class I (pMHC-I) multimer complexes. The method includes: a) incubating a plurality of MHC class I heavy chains, a plurality of β2-microglobulins, and a plurality of placeholder peptides under conditions where the plurality of MHC class I heavy chains, β2-microglobulins and placeholder peptides form a plurality of p*MHC-I complexes; b) contacting the plurality of p*MHC-I complexes with a plurality of dipeptides and chaperones, where the chaperones are provided at a molar ratio of chaperone to p*MHC-I complex of less than 1:1, thereby creating a peptide receptive MHC-I complex; c) attaching the plurality of peptide receptive MHC-I complexes to multimer backbones, thereby forming a plurality of peptide receptive MHC-I multimers; and d) contacting the plurality of peptide receptive MHC-I multimers with a plurality of peptides of interest, thereby forming a plurality of pMHC-I multimer complexes.

In a fourth aspect, provided herein is an alternative method of making a plurality of peptide-MHC class I (pMHC-I) multimer complexes, each complex comprising an MHC class I multimer and a peptide of interest. The method includes: a) providing a plurality of placeholder peptide-MHC class I (p*MHC-I) complexes, wherein each p*MHC-I complex comprises an MHC class I heavy chain, an β2-microglobulin, and a placeholder peptide; b) contacting the plurality of p*MHC-I complexes with a plurality of chaperones, dipeptides, multimer backbones, and peptides of interest under conditions to form a plurality of peptide-MHC class I multimer complexes, thereby forming a plurality of pMHC-I multimer complexes; where the chaperones are provided at a molar ratio of chaperone to p*MHC-I complex of less than 1:1, and c) recovering the plurality of peptide-MHC class I multimer complexes.

In certain embodiments, the chaperones include TAPBPR.

In other embodiments, the molar ratio of chaperone to p*MHC-I is less than 1:2, less than 1:10, less than 1:50, less than 1:100, less than 1:500, or less than 1:1000.

In other embodiments, the amount of chaperone added is sufficient to convert at least 95% of the MHC class I molecules to peptide receptive MHC-I complexes.

In other embodiments, the dipeptides include glycyl-methionine or glycyl-phenylalanine.

In other embodiments, all the peptides in the plurality of the peptides of interest have the same sequence.

In other embodiments, at least some or all of the peptides in the plurality of the peptides of interest have different sequences.

In other embodiments, at least some or all of the peptides in the plurality of the peptides of interest are tumor antigen peptides, viral peptides, or bacterially derived peptides.

In other embodiments, some or all of the pMHC-I complexes are attached to a barcode DNA oligo.

In other embodiments, the multimer backbones are selected from streptavidin, avidin and dextran backbones, including particular examples where the multimers are tetramers.

In other embodiments, the p*MHC-I complexes are biotinylated.

In still other embodiments free chaperones are removed after the chaperones convert the p*MHC-I complexes to activated pMHC-I complexes, including particular examples where the free chaperones are removed by spin column dialysis.

In a fifth aspect, provided herein is a peptide receptive MHC-I complex made by the methods above.

In a sixth aspect, provided herein is a composition comprising a) a plurality of MHC class I heavy chains, a plurality of β2-microglobulins, and a plurality of placeholder peptides and b) a plurality of chaperones, where the molar ratio of chaperones to peptide-deficient MHC class I molecules is less than 1:1.

In certain embodiments, the molar ratio of chaperones to peptide-deficient MHC class I molecules is less than 1:2, less than 1:10, less than 1:50, less than 1:100, less than 1:500, or less than 1:1000.

In other embodiments, molar ratio of MHC class I heavy chains to β2-microglobulins is less than 1:3.

In other embodiments, the composition comprises a plurality of complexes, each complex comprising an MHC class I heavy chain and an β2-microglobulin and where the complex is in a configuration that can accept a peptide of interest (e.g., it is a peptide receptive MHC-I complex).

In other embodiments, some or all of the complexes further comprise a placeholder peptide.

In other embodiments, some of the complexes further comprise a chaperone, such as, in one particular example, TAPBPR.

In a seventh aspect, provided herein is a composition comprising a plurality of complexes. The complexes each comprise an MHC class I heavy chain and an β2-microglobulin. Each complex is in a configuration that can accept a peptide of interest, and the composition was subjected to a process that removes free chaperones.

In certain embodiments, the process removes at least 90%, at least 95%, at least 98%, at least 99%, at least 99.9% or 100% of the free chaperones.

In other embodiments, the process comprises dialysis, including, for example, spin column dialysis.

DB2/38830762.1 15 NS: non-specific gp29 peptide (sequence YPNVNIHNF (SEQ ID NO: 41)), used as a negative control. Data shown is representative of triplicate gel assays.

Figure 1:
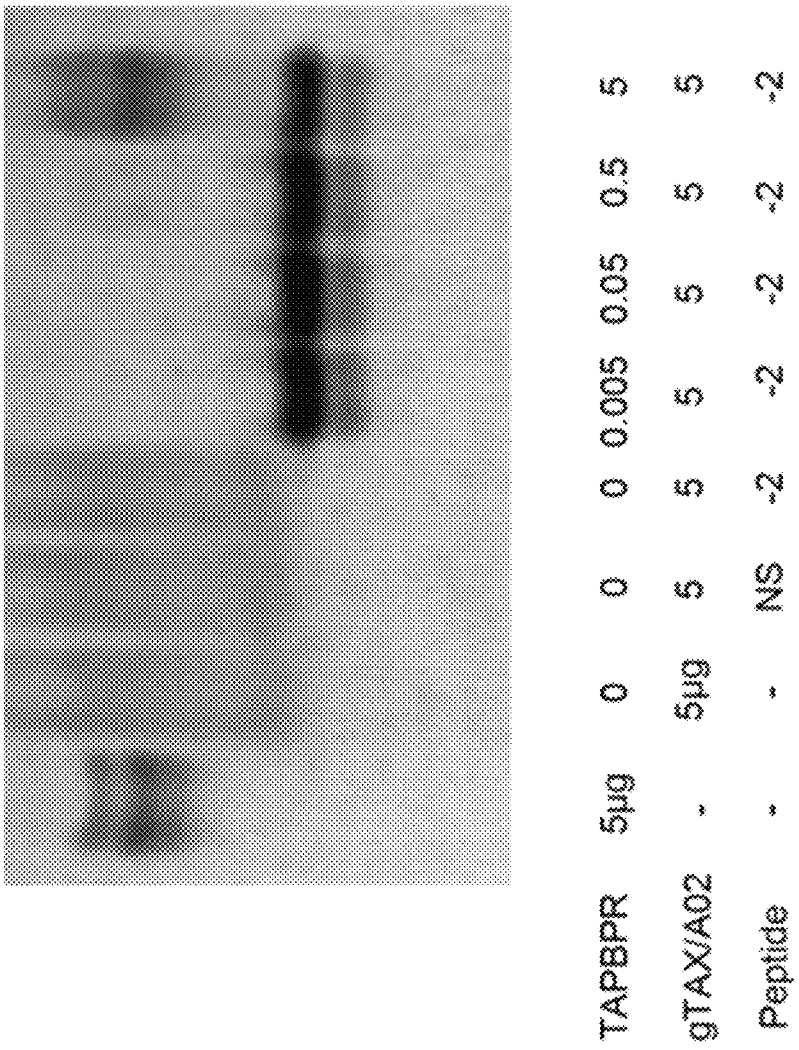
FIG. 1 shows the results of a native gel electrophoresis analysis of peptide exchange using varying amounts of TAPBPR (0.005 μg to 5 g), monitoring the formation of exchanged pMHC-I complexes of different electrophoretic mobilities. Each indicated reaction was incubated overnight at 4° C. in the presence of 10-fold molar excess of a high affinity peptide (sequence SLLDDAFAL (SEQ ID NO:45), net charge of −2 at neutral pH), and a fixed concentration of gTAX/HLA-A*2:01.
Figure 2:
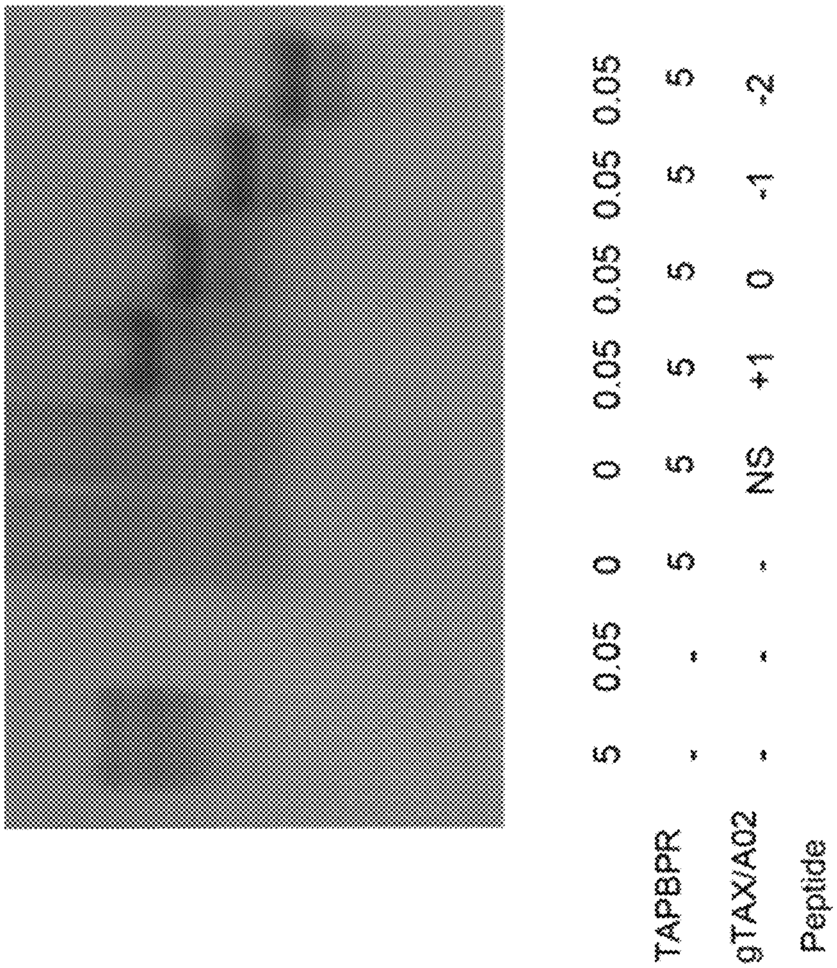
FIG. 2 shows the results of a native gel electrophoresis analysis of TAPBPR exchange on gTAX/HLA-A*02:01 of four different high affinity peptides with net charges at neutral pH ranging from +1 to −2 (sequences RVADYIVKV (SEQ ID NO:46), ALFPERITV (SEQ ID NO: **), AIADISYSV (SEQ ID NO:44), SLLDDAFAL (SEQ ID NO:45), as indicated. 12% polyacrylamide native gels were run at 90V for 5 hrs at 4° C. before visualization with InstantBlue (Expedeon).

All protein samples used in FIGS. 1 and 2 were derived from the same peptide exchange experiment, and the gels were processed in parallel. Note that while the units shown in FIG. 1 and FIG. 2 show masses of TAPBPR and the p*MHC-I complexes, TAPBPR and p*MHC-I are of a similar molecular weight so the molar ratio is approximately equivalent to the mass ratio.

Figure 3:
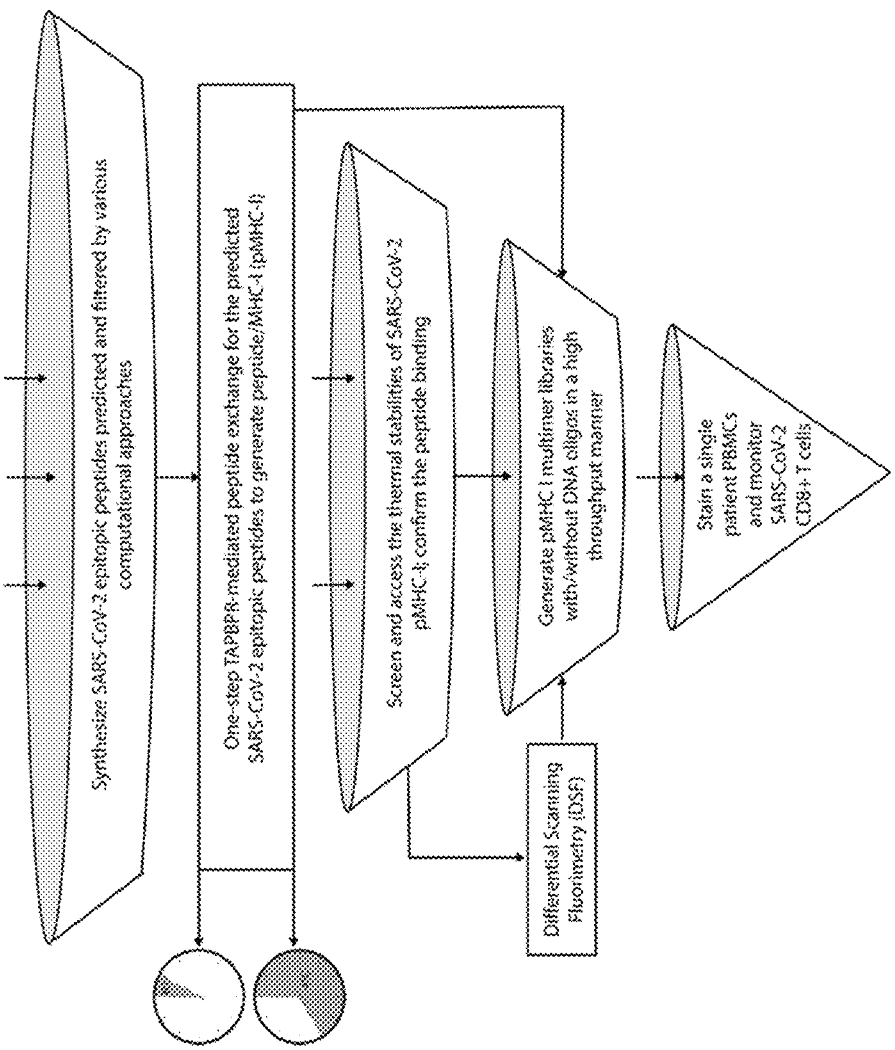

FIG. 3 is a workflow of translating epitopic peptide predictions into pMHC-I multimers, which can be used to monitor SARS-CoV-2-specific CD8 T cell responses in COVID-19 patients. SARS-CoV-2 peptide candidates compete for binding on MHC-I molecules refolded with the placeholder peptide gTAX. The reaction is catalyzed by the molecular chaperone TAPBPR. Each exchange reaction is incubated for one hour at room temperature, and the thermal stabilities of the resulting SARS-CoV-2 pMHC-I molecules are accessed using a Differential Scanning Fluorimetry (DSF) assay, to confirm that peptide exchange has occurred. Selected SARS-CoV-2 pMHC-I are then loaded onto fluorophore-label streptavidin or Klickmers® with optional DNA oligo barcoding.

Figure 4A:
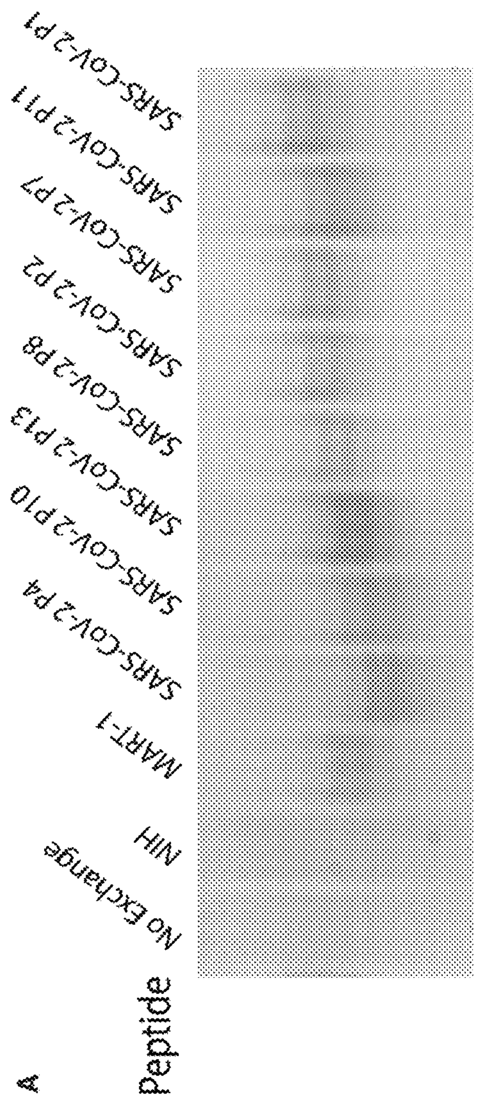

FIG. 4A is a native gel electrophoretic mobility shift assay of pMHC-I molecules, generated by overnight catalytic TAPBPR exchange for SARS-CoV-2 epitopic peptides 4, 10, 13, 8, 2, 7, 11, and 1 with net charges at neutral pH ranging from +1 to −2 (Sequence: NLNESLIDL (SEQ ID NO:8) (P4), ILLLDQALV (P10), KLPDDFTGCV (SEQ ID NO:17) (P13), GMSRIGMEV (SEQ ID NO:12) (P8), VLNDILSRL (SEQ ID NO:6) (P2), LLLDRLNQL (SEQ ID NO:11) (P7), SLPGVFCGV (SEQ ID NO: 15) (P11)). pMHC-I/gTAX without peptide exchange and with the exchange of non-specific peptide NIH (Sequence: YPNVNIHNF (SEQ ID NO:41)) were used as negative controls. Irrelevant high-affinity peptide MART-1 (Sequence: ELAGIGILTV (SEQ ID NO:38)) was used as a positive control.

Figure 4B:
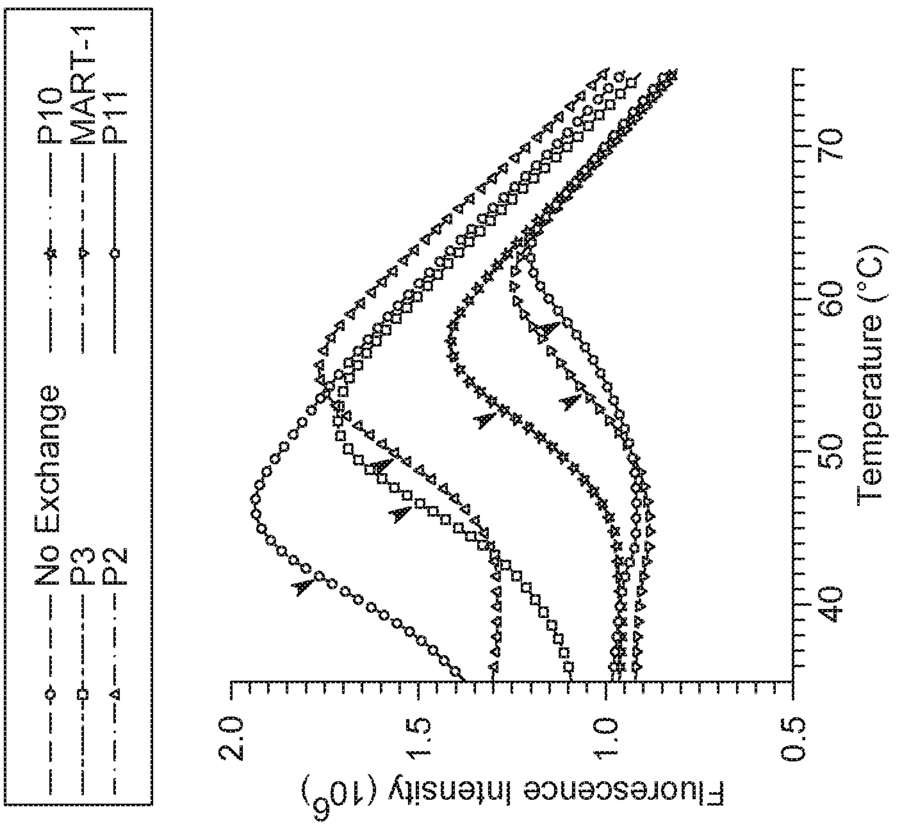

FIG. 4B shows the results of overlaid differential scanning fluorimetry (DSF) temperature profile of pMHC-I/gTAX and exchanged pMHC-I/MART-1SARS-CoV-2 epitopic peptide 3, 2, 10, and 11. Arrowheads point towards the maximum slope for each profile, thereby indicating the approximate Tm.

Figure 4C:
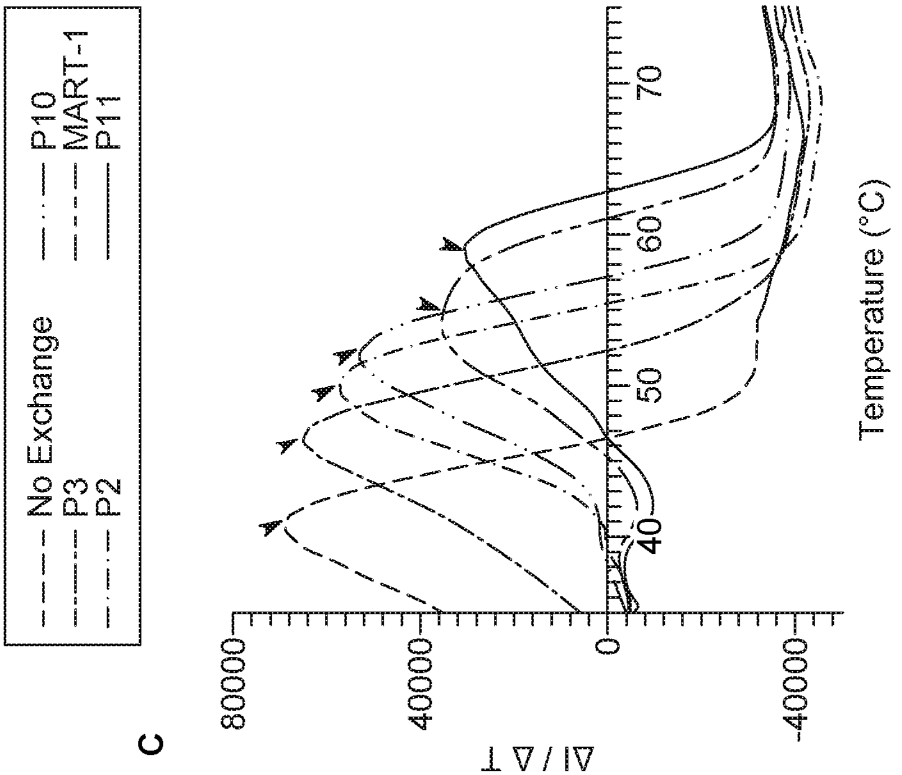

FIG. 4C shows a derivation of the melting curves from the conventional DSF data for TAPBPR exchanged MART-1, SARS-CoV-2 epitopic peptide 3, 2, 10, and 11 each bound to HLA-A*02:01 and pMHC-I/gTAX (black) without peptide.

Figure 5A:
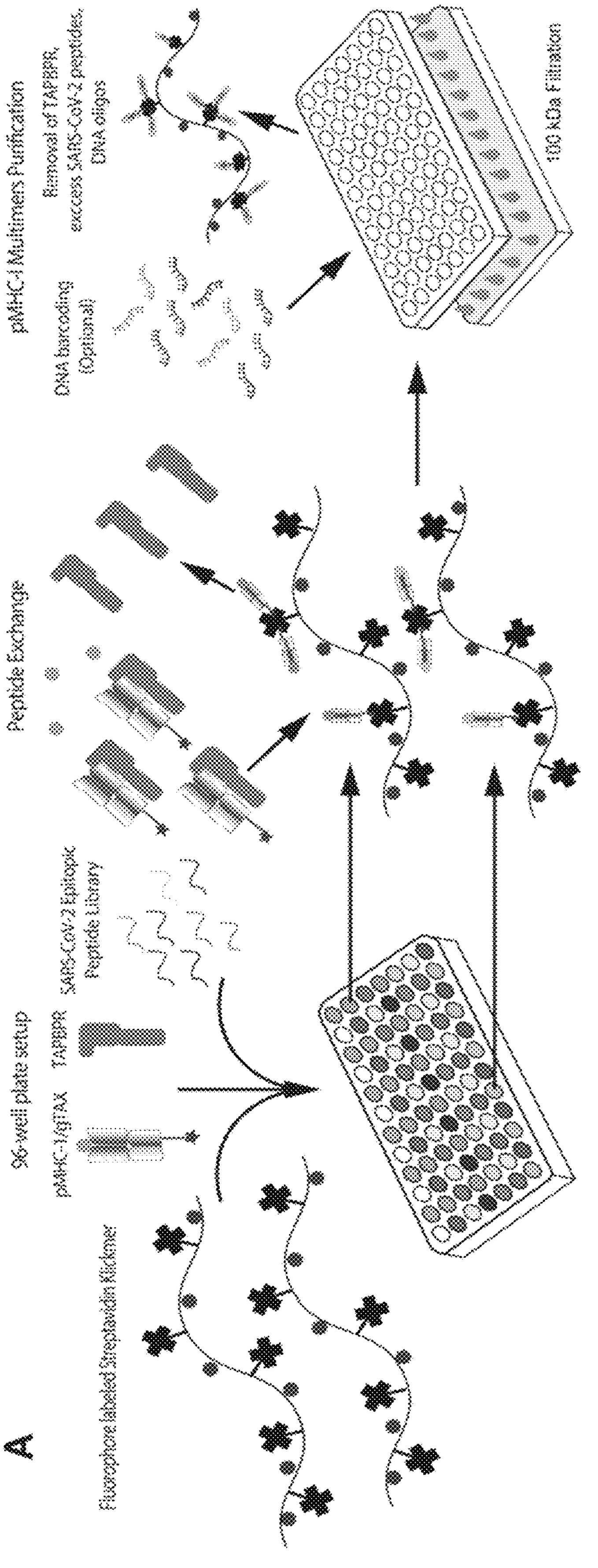

FIG. 5A illustrates an experimental protocol where SARS-CoV-2 peptides, pMHC-I/gTAX, TAPBPR, and fluorophore-labeled Klickmer® arrayed on a 96-well plate at a molar ratio of 300:30:3:1. TAPBPR associates with pMHC-I/gTAX to release the placeholder gTAX peptide, and dissociates from MHC-I upon binding of high-affinity SARS-CoV-2 peptides. pMHC-I molecules are linked to Klickmers® via a tight streptavidin-biotin bond to form Dextramers®. The mixture is washed with 1000 volume of PBS, and TAPBPR, excess peptides are removed through centrifugation for 5 min at 500 g.

Figure 5B:
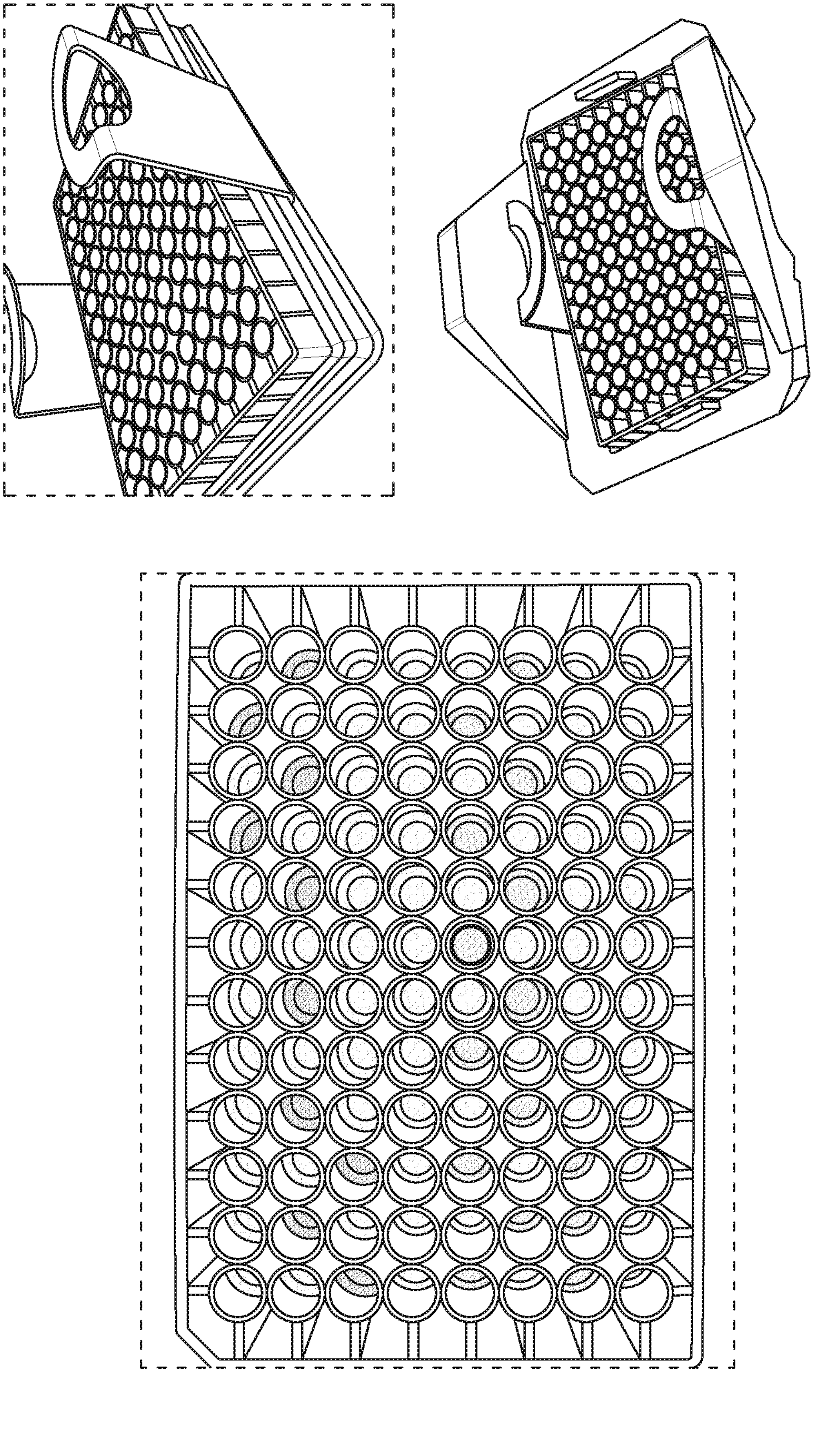

FIG. 5B is a 96-well filter plate with a membrane cut-off of 100 kDa containing peptide exchange reactions loaded in each well. The filter plate is assembled with the black flow-through plate and loaded into the Beckman SX4750 swing-bucket rotor for centrifugation.

DETAILED DESCRIPTION

Overview

High-throughput screening strategies using large arrays of peptide-MHC class I multimers can allow for the large scale identification of antigen specific T cells and/or peptide antigens that bind to particular MHC class I alleles (e.g., tumor antigens, viral antigens). Identification of such antigen specific T cells and/or antigens can in turn lead to the understanding of the pathogenesis of particular diseases, as well as the development of novel therapies.

Such high-throughput screens, however, are limited by the ability to produce large collections of peptide-MHC class I multimers. The instability of peptide deficient MHC class I molecules, for example, makes large scale production of peptide-MHC class I multimers using such MHC class I molecules difficult. While conditional ligands have been used for large scale production of peptide-MHC class I multimers, such conditional ligands are limited due to sample aggregation, precipitation during the photolysis/peptide exchange step, and, in some cases, instability of the conditional ligand leading to high background levels of exchange. As such, there remains a need for new methods of making peptide-MHC class I multimer complex libraries.

Provided herein are stable, soluble MHC class I complexes in a configuration to accept a peptide of interest (called peptide receptive MHC-I complexes herein) and methods of making such compositions. Such peptide receptive MHC-I complexes can be used for production of large collections of peptide-MHC class I (pMHC-I) multimers (e.g., up to 10,000 different specificities), which can then in turn be used in high throughput screens for immune profiling towards disease diagnosis and for the development of new therapies. The peptide receptive MHC-I complexes provided herein are advantageously stable and can be stored for long periods of time prior to their use in making pMHC-I complexes and/or pMHC-I multimers. Specifically as described herein, the peptide receptive MHC-I complexes are made by contacting a complex comprising an MHC-I light chain, an MHC-I heavy chain, and a placeholder peptide (called a p*MHC-I herein) with a catalytic amount of a molecular chaperone. A catalytic amount of chaperone is any amount where the molar ratio of chaperone to p*MHC-I is less than 1:1. The molar ratio can be any such ratio of chaperone to p*MHC-I including a ratio less than 1:2, less than 1:10, less than 1:50, less than 1:100, less than 1:500, less than 1:1000, or less than 1:1000 provided that there is sufficient chaperone present to convert at least 50%, at least 60%, at least 70%, at least 75%, at least 80%, at least 85%, at least 90%, at least 95%, or 100% of the p*MHC-I to peptide receptive MHC-I complexes. Note that the molecular weight of a p*MHC-I is similar to the molecular weight of the TAPBPR chaperone and so the molar ratio is approximately equivalent to the mass ratio.

Peptide Receptive MHC-I Complexes

In one aspect, provided herein is a composition that includes a plurality of peptide receptive MHC-I complexes and a plurality of chaperones and where the molar ratio of chaperone to p*MHC-I is less than 1:1. Such compositions are advantageously stable and can be stored for long periods of time in solution prior to use, for example, in making peptide-MHC class I multimer complexes, as described herein. In other aspects, the compositions include peptide receptive MHC-I complexes, but the composition has been subjected to a process that removes free chaperones, such as a dialysis process.

As used herein, an "MHC class I," "Major Histocompatibility Complex class I," "MHC-I" and the like all refer to a member of one of two primary classes of major histocompatibility complex (MHC) molecules (the other being MHC class II) that are found on the cell surface of all nucleated cells in the bodies of jawed vertebrates. MHC class I molecules function to display peptide fragments of antigen to cytotoxic T cells; resulting in a response from the immune system against a particular antigen displayed with the help of an MHC class I molecule.

MHC class I molecules are heterodimers that consist of two polypeptide chains, the heavy chain (also called the α-chain) and the light chain (also called β2-microglobulin). The two chains are linked noncovalently via an interaction between the light chain and the α3 domain of the heavy chain and the floor of the α1/α2 domain of the heavy chain. In humans, only the heavy chain is polymorphic and encoded by a HLA gene, while the light chain is effectively invariant within a species and encoded by the beta-2 microglobulin gene. The α3 domain is plasma membrane-spanning and interacts with the CD8 co-receptor of T-cells. The α3-CD8 interaction holds the MHC-I molecule in place while the T cell receptor (TCR) on the surface of the cytotoxic T cell binds its syngeneic MHC-I ligand (or matched, in the sense that both the TCR and MHC-I are encoded in the same germline), and checks the coupled peptide for antigenicity. The α1 and α2 domains of the heavy chain fold to make up a groove for peptides to bind. MHC class I molecules bind peptides that, in most cases, are 8-10 amino acids in length.

In mice, MHC class I is called the "H-2 complex" or "H-2" and include the H-2D, H-2K and H-2L subclasses. In humans, MHC class I molecules include the highly polymorphic human leukocyte antigens HLA-A, HLA-B, HLA-C and the less polymorphic HLA-E, HLA-F, HLA-G, HLA-K and HLA-L. Each human leukocyte antigen (e.g., HLA-A) includes multiple alleles. For example, HLA-A includes over 2430 known alleles. In some embodiments, the purified peptide receptive MHC-I complex includes an HLA-A. In certain embodiments, the purified peptide receptive MHC-I-complex includes an HLA-B. In other embodiments, the purified peptide receptive MHC-I complex includes an HLA-C. In an exemplary embodiment, the peptide receptive MHC-I complex includes an HLA-A02 allele. In other embodiments, the peptide receptive MHC-I complex includes an H-2. In certain embodiments, the H-2 is an H-2D, H-2K or H-2L. In exemplary embodiments, the H-2 is a particular allele of H-2D, H-2K, or H2L, such as H-2$D^d$ or H-2$L^d$.

As described above, peptide receptive MHC-I complexes are created from placeholder peptide-MHC-I complexes (p*MHC-I) through the action of a chaperone. The chaperone can be any chaperone. In some embodiments, the chaperone is the Tapasin Binding Protein Related (TAPBPR) chaperone. In an exemplary embodiment, the peptide receptive MHC-I complex includes a TAPBPR chaperone and an HLA-A MHC class-I molecule. In further embodiments, the HLA-A is HLA-A02. Further disclosed herein is the surprising result that a chaperone such as TAPBPR can act catalytically upon p*MHC-I to yield a peptide receptive MHC-I complex. This means that the reaction that creates a peptide receptive MHC-I complex from a p*MHC-I can be performed even when the molar ratio of chaperone to p*MHC-I is less than 1:1. The molar ratio can be any such ratio of chaperone to p*MHC-I including a ratio less than 1:2, less than 1:10, less than 1:50, less than 1:100, less than 1:500, less than 1:1000, less than 1:5000, or less than 1:10,000 provided that there is sufficient chaperone present to convert at least 50%, at least 60%, at least 70%, at least 75%, at least 80%, at least 85%, at least 90%, at least 95%, or 100% of the p*MHC-I to peptide receptive MHC-I complexes.

Peptide receptive MHC-I complexes compositions are advantageously highly stable and soluble. In some embodiments, the peptide receptive MHC-I complexes can be stored at concentrations of up to 50, 100, 150, 200, 250, 300, 350, or 400 M in solution without precipitation at 4° C. In certain embodiments, the peptide receptive MHC-I complexes are completely soluble and remain peptide receptive in solution at a concentration of up to 400 μM at 4° C. for up to 1 month, 2 months, 3 months, 4 months, 5 months, 6 months, 7 months, 8 months, 9 months, 10 months, 11 months, or a year. The stability of peptide receptive MHC-I complexes can be measured, for example, using differential scanning fluorimetry techniques. In certain embodiments, the peptide receptive MHC-I complexes are stored at −80° C. In particular embodiments, the peptide receptive MHC-I complexes are lyophilized.

In another aspect, provided herein is a method of making peptide receptive MHC-I complexes. To make such complexes, a plurality of MHC class I heavy chains, β2-microglobulins and placeholder peptides are incubated under conditions wherein the MHC class I heavy chain, the β2-microglobulin and the placeholder peptide form placeholder peptide-MHC class I (p*MHC-I) complexes. The p*MHC-I complexes are then contacted with a dipeptide and chaperone and then changed into peptide receptive MHC-I complexes that can accept a peptide of interest.

In the first step of making the peptide receptive MHC-I complex, MHC class I heavy chains, β2-microglobulins and placeholder peptides are incubated under conditions wherein the MHC class I heavy chain, the β2-microglobulin and the placeholder peptide refold to form a p*MHC-I complex. MHC class I heavy chains and light chains can be obtained using any method known to one of skill in the art. For example, nucleic acids encoding known MHC class I heavy chains and light chains can be integrated into one or more expression vectors that are in turn transformed into a suitable host for expression (e.g., *E. coli*). MHC class I heavy chains and light chains produced by such host cells can then be isolated and purified for use with the disclosed methods.

In some embodiments, the heavy chain, light chain and placeholder peptide are incubated in a refolding buffer that favors the formation of the p*MHC-I complex. In an exemplary embodiment, the refolding buffer includes arginine-HCl, EDTA, reduced oxidized L-glutathione, and Tris base. The heavy chain and light chain can be present at any ratio that favors the formation of the p*MHC-I complex. In certain embodiments, the MHC class I heavy chains and light chains are incubated at a 1:1, 1:2, 1:3, 1:4, 1:5 ratio of heavy chain to light chain. In an exemplary embodiment, the MHC class I heavy chains and light chains are incubated at a ratio of 1:3 in the presence of the placeholder polypeptide. The MHC class I heavy chain and light chains can be incubated with the placeholder peptide in the refolding buffer for at least about 12 hours, at least about 18 hours, at least about 24 hours, at least about 2 days, at least about 3 days, at least about 4 days, at least about 5 days, at least about 6 days or at least about a week or more to obtain properly folded p*MHC-I complexes. In some embodiments, the MHC class I heavy chain, light chain and placeholder peptides are incubated for 1 to 4 days. In certain embodiments, this first step is carried out at approximately 3° C. to 10° C. In an exemplary embodiment, the refolding of the MHC class I heavy chain and light chains with the placeholder peptide is carried out at 4° C.

Suitable placeholder peptides that can be used in this first step include, for example, modified versions of peptides known to bind to the particular MHC class I allele included in the peptide receptive MHC-I complex. Such placeholder polypeptides have been modified to have a lower binding affinity to the particular MHC class I molecule compared to the known polypeptide. In some embodiments, the placeholder polypeptide is a N-terminal truncated version of a known polypeptide that binds to the MHC class I allele (e.g., an HLA-A02). For example, a known peptide that binds to HLA-A02 is the HTLV-1 epitope TAX11-19, having the amino acid sequence LLFGYPVYV (SEQ ID NO:1). As such, a suitable placeholder peptide that can be used in making the disclosed peptide receptive MHC-I complexes has the amino acid sequence LFGYPVYV (SEQ ID NO:40). In some embodiments, wherein the MHC class I is HLA-A02, examples of the placeholder peptide can be LFGYPVYV (SEQ ID NO: 40) (gTAX), Ac-LLFGYPVYV (SEQ ID NO:2) (N-terminally acetylated TAX), or ILFGYPVYV (SEQ ID NO:3) (first residue is a D-leucine). In other embodiments, where the MHC class I allele is mouse H-2Dd, the placeholder peptide can have the sequence GPGRAFVTI (SEQ ID NO: 4). (gP18-I10). In still other embodiments, where the MHC class I is mouse H-2Ld, the placeholder peptide can have the sequence QLSPFPFDL (SEQ ID NO:42) (QL9). In other embodiments where the MHC class I is human HLA-A*24:02, the placeholder peptide can have the sequence YPLTFGWCF (SEQ ID NO:43). In still other embodiments, where the MHC class I his human HLA-A*68:02, the placeholder peptide can have the sequence LFGYPVYV (SEQ ID NO:40) (gTAX).

Placeholder peptides are typically at least 8 amino acids long. In some embodiments, the placeholder polypeptide is at least 8, 9, 10, 11, 12 or 13 amino acids long. In particular embodiments, the polypeptide is 8, 9, 10, 11, 12 or 13 amino acids long. The interaction between a placeholder peptides and an MHC class I allele generally has a melting temperature (Tm) of less than 50° C. The Tm can be less than 49° C., less than 48° C., less than 47° C., less than 46° C., less than 45° C., less than 44° C., less than 43° C., less than 42° C., less than 41° C., or less than 40° C.

In the second step, the p*MHC-I complexes are incubated in the presence of a dipeptide and chaperones. As described above, the chaperone acts catalytically on the p*MHC-I complex, changing it to a peptide receptive MHC-I capable of accepting a peptide of interest. Also as described above, the peptide receptive MHC-I complex is stable and can be stored for long periods of time prior to loading with one or more peptides of interest and formation of multimers (e.g., tetramers).

In some embodiments, the chaperone is a Tapasin Binding Protein Related (TAPBPR). TAPBPR protein includes a signal sequence, three extracellular domains comprising a unique membrane distal domain, an IgSF (immunoglobulin superfamily) V domain and an IgC1 domain, a transmembrane domain, and a cytoplasmic region. See, e.g., Boyle et al., PNAS 110 (9) 3465-3470 (2013), incorporated by reference herein. TAPBPR can be made by any method known in the art, including those described in Morozov et al, PNAS 113, E1006-E1015 (2016) which is incorporated by reference herein, particularly for its teaching of methods of making TAPBR chaperones. In other embodiments, the chaperone is Tapasin. In some embodiments, the chaperone (e.g., TAPBR) is incubated with the p*MHC-I complex and dipeptide at a ratio of less than 1:1 chaperone to p*MHC-I complex, including less than 1:2, less than 1:5, less than 1:10, less than 1:50, less than 1:100, less than 1:500, or less than 1:1000 provided that there is sufficient chaperone present to convert at least 50%, at least 60%, at least 70%, at least 75%, at least 80%, at least 85%, at least 90%, at least 95%, or 100% of the p*MHC-I to peptide receptive MHC-I complexes. In an exemplary embodiment, the dipeptide is glycyl-methionine or glycyl-phenylalanine.

The incubation of the p*MHC-I, chaperone and dipeptide can last for at least 1 hour, 2 hours, 3 hours, 4 hours, 5 hours and 6 hours. Following incubation, the resulting peptide receptive MHC-I complexes can be isolated by size exclusion chromatography (SEC) and confirmed using any technique known in the art, including, for example, liquid chromatography-mass spectrometry techniques.

In some embodiments, the MHC class I of the p*MHC-I (and by extension the peptide receptive MHC-I) is an HLA-A. In an exemplary embodiment, the HLA-A is HLA-A02. In other embodiments, the MHC class I of the p*MHC-I is an H-2. In exemplary embodiments, the H-2 is H-2Dd or H-2Ld.

In some embodiments, the MHC class I is a variant MHC class I that includes one or more mutations that reduces MHC class I binding affinity for TAPBR chaperone. Such a mutation advantageously facilitates subsequent peptide loading and/or peptide-MHC class I multimer complex production as described below. In some embodiments, the variant MHC class I includes one or more mutations in the α3 domain of the heavy chain that reduces MHC class I binding affinity for TAPBR chaperone. In certain embodiments, the MHC class I heavy chain is mouse H-2. In further embodiments, the H-2 is a variant of H-2$D^d$ or H-2$L^d$ that includes an amino acid substitution at M228 in the α3 domain of the heavy chain. In particular embodiments, the M228 substitution is a M228N, M228Q, M228S, M228T or M228Y substitution.

In certain embodiments, either or both of the MHC class I heavy chain and β2-microglobulin molecules in the peptide receptive MHC-I composition are biotinylated. In an exemplary embodiment, the MHC-I heavy chain or light chain is biotinylated using a C-terminal BirA tag with any method known to one of skill in the art, including use of a biotin ligase. In an exemplary embodiment, the biotinylation occurs after the purification of the p*MHC-I complex. Biotinylation of peptide receptive MHC-I complex monomers allows for the attachment of such monomers to backbones (e.g., streptavidin or dextran) to form multimers (e.g., peptide receptive MHC-I complex tetramers) that can be used in various methods described herein.

Peptide-MHC Class I Complexes

The purified peptide receptive MHC-I complexes can be subsequently loaded with a peptide of interest. In this step, the purified peptide receptive MHC-I complexes are incubated in the presence of the peptide of interest. Without being bound by any particular theory of operation, it is believed that when present in molar excess of the peptide receptive MHC-I complexes, the peptide of interest is loaded onto the MHC class I, thereby forming a peptide-MHC class I complex that includes the peptide of interest (pMHC-I). The resulting pMHC-I can further be used to form multimers, for example, tetramers, pentamers or Dextramers®. Uses for such multimers (e.g., the identification of antigen specific T cells) are further described herein and are known to one of skill in the art.

In some embodiments, the peptide of interest is incubated at a molar excess of at least 2, 5, 10, 15, 20, 25, 30, 35, 40, 45, 50, 75 or 100 times to the peptide receptive MHC-I. In an exemplary embodiment, the peptide of interest is incubated at a molar excess of 50 times to the peptide receptive MHC-I complex. Such incubations can be carried out at room temperature for at least 30 minutes, 1 hour, 2 hours, 5, hours, 10 hours, 15 hours, 20 hours, 24 hours, two days, four days, or longer.

In some embodiments, the peptide of interest is incubated at a molar excess of at least 2, 5, 10, 15, 20, 25, 30, 35, 40, 45, 50, 75 or 100 times to the peptide deficient-MHC class I in the MHC class I/chaperone composition. In an exemplary embodiment, the peptide of interest is incubated at a molar excess of 50 times to the peptide deficient-MHC class I/chaperone complex. Such incubations can be carried out at room temperature for at least 30 minutes, 1 hour, 2 hours, 5, hours, 10 hours, 15 hours, 20 hours, 24 hours, two days, four days, or longer.

Peptides of interest are typically 8 to 13 amino acids in length. In some embodiments, the peptide of interest is an antigen. In an exemplary embodiment, the peptide of interest is a tumor antigen, viral antigen, bacterial antigen, or a self-antigen that results in an autoimmune disease. Tumor antigen peptides, viral antigen peptides, bacterial antigen peptides, and self-antigen peptides in the context of the pMHC-I and multimer complexes described herein can be useful, for example, in the identification of T cells reactive to the antigen of interest.

Purification of the pMHC-I complexes from the released chaperone can be carried out using size exclusion chromatography (SEC). The newly formed pMHC-I can be confirmed using any technique known in the art, including, for example, liquid chromatography-mass spectrometry techniques. Alternatively, the pMHC-I complexes can be labeled (e.g. with biotin and or a Histidine×6 tag) and purified based on differential binding of the label to its ligand (e.g. streptavidin or nickel ion).

In some embodiments, the MHC class I allele in the pMHC-I complex is an HLA-A. In an exemplary embodiment, the HLA-A is HLA-A02. In one embodiment, the pMHC-I is biotinylated. In other embodiments, the MHC class I of the peptide-MHC class I complexes is an H-2. In exemplary embodiments, the H-2 is H-2Dd or H-2Ld. In certain embodiments, the H-2 is a variant H-2Dd or H-2Ld that includes an amino acid substitution at M228 in the α3 domain of the heavy chain. In particular embodiments, the M228 substitution is a M228N, M228Q, M228S, M228T or M228Y substitution. Such a mutation advantageously reduces H-2 binding affinity for TAPBR chaperone, thereby facilitating subsequent peptide loading and/or peptide-MHC class I multimer complex production as described below.

Peptide-MHC Class I Multimer Complexes

Peptide-MHC class I complexes (pMHC-I) made using the subject methods described herein can undergo further multimerization to form multimers that include two or more of the pMHC-I complexes (i.e., pMHC-I multimers.) In certain embodiments, the multimers include 2, 3, 4, 5, 6, 7, 8, 9 or 10 pMHC-I molecules.

In some embodiments, pMHC-I multimers can be produced by attachment of biotinylated pMHC-I to a backbone (e.g., a streptavidin, avidin or dextran backbone), thereby forming a pMHC-I multimer. In an exemplary embodiment, the biotinylation occurs following the purification of p*MHC-I monomers and prior to the formation of peptide receptive MHC-I complexes. In some embodiments wherein large scale production of pMHC-I multimer libraries is desired, aliquots of the peptide receptive MHC-I complexes are incubated with various peptides of interest and allowed to undergo peptide loading to form pMHC-I. The resulting pMHC-I are then multimerized in the presence of a suitable backbone to form pMHC-I multimers (e.g., tetramers, pentamers, Dextramers®). In some embodiments, the backbone is a streptavidin backbone. In other embodiments, the backbone is an avidin backbone. In still other embodiments, the backbone is a dextran backbone.

In other embodiments, the peptide receptive MHC-I complexes are biotinylated and then attached to a backbone (e.g., a streptavidin, avidin or dextran backbone), thereby forming peptide receptive MHC-I complex multimers (e.g., tetramers). Such peptide receptive MHC-I complex multimers can be used for the large scale production of pMHC-I multimers comprising one or more peptides of interest by contacting the peptide receptive MHC-I complex multimers with the one or more peptides of interest. For example, in one embodiment, aliquots of the peptide receptive MHC-I complex multimers are contacted with different peptides of interest, thereby forming a library of pMHC-I multimers. The resulting loaded pMHC-I multimers can be washed to remove any free chaperones, labels (e.g., nucleic acid barcodes) and/or peptides of interest. Following such a washing step, the pMHC-I multimers can be stored (e.g., 4° C. for several weeks) or used immediately. In some embodiments, the free chaperones, labels and/or peptides of interest are removed by spin column dialysis.

In some embodiments, peptide-MHC class I multimer complexes are made by contacting subject p*MHC-I complexes with a plurality of chaperones, dipeptides, multimer backbones, and peptides of interest under conditions to form a plurality of peptide-MHC class I multimer complexes. In certain embodiments, the molar ratio of chaperone to p*MHC-I complex provided is less than 1:1.

In some embodiments, the pMHC-I multimer is a dimer. In some embodiments, the pMHC-I multimer is a trimer. In preferred embodiments, the pMHC-I multimer is a tetramer. In another embodiment, the multimer is a pentamer or Dextramer®. Dextramers® include ten or more pMHC-I attached to a dextran backbone. Dextramers® allow for the detection, isolation, and quantification of antigen specific T-cell populations due to an improved signal-to-noise ratio not present in prior generations of multimers. See, e.g., Bakker and Schumacher, *Current Opinion in Immunology* 17(4): 428-433 (2005); and Davis et al., *Nature Reviews Immunology* 11:551-558 (2011).

In some embodiments, the backbone is conjugated with a detectable label (e.g., a fluorophore or a radiolabel) that allow the multimer to be detected in various applications. In certain embodiments, the detectable label is as fluorophore. See, e.g., Nepom et al., *J Immunol* 188 (6) 2477-2482 (2012). In one embodiment, the detectable label is a radiolabel. In certain embodiments, the backbone includes a barcode (e.g., a nucleic acid barcode) that allows the pMHC-I multimer to be used in large scale high throughput processes. See, e.g., Bentzen et al., *Nature Biotechnology* 34(1): 1037-1045 (2016). In an exemplary embodiment, unique barcodes are used for each of the different peptides of interest included in the pMHC-I multimers, thereby allowing for the tracking, sorting and identification of particular pMHC-I multimers in high throughput applications. In particular embodiments, each barcode includes a unique nucleotide sequence.

In some embodiments, the pMHC-I multimer complex is coupled to a toxin (e.g., saporin). Such pMHC-I multimer conjugates can be used to modulate or deplete specific T cell populations. See, e.g., Maile et al., *J. Immunol.* 167:3708-3714 (2001); and Yuan et al., *Blood* 104:2397-2402 (2004).

pMHC-I Multimer Libraries

The methods provided herein allow for the large scale production of stable peptide receptive MHC-I complexes that can in turn be used to produce pMHC-I multimer libraries that include a plurality different peptides of interest for high throughput applications.

In one aspect provided herein, peptide receptive MHC-I complexes (monomers or multimers) are used to form a pMHC-I multimer library that includes pMHC-I multimers having different peptides of interest. Such pMHC-I multimer libraries can be made by contacting aliquots of peptide receptive MHC-I complex multimers with different peptides of interest or by contacting aliquots of peptide receptive MHC-I complex monomers with different peptides of interest followed by multimerization of the resulting pMHC-I monomers. In some embodiments, a pMHC-I multimer library is made by incubating subject p*MHC-I complexes with a plurality of chaperones, dipeptides, multimer backbones, and different peptides of interest under conditions to form the pMHC-I multimer library. In certain embodiments, the molar ratio of chaperone to p*MHC-I complex provided is less than 1:1. In some embodiments, the peptides of interest are different peptides from an antigen of interest. In certain embodiments, the antigen of interest is a tumor antigen, viral antigen, bacterial antigen, or self antigen.

In some embodiments, pMHC-I monomers that include the same peptide of interest are attached to backbones to form pMHC-I multimers and the step is performed for a plurality of pMHC-I monomers that include a library of different peptides of interest. In some embodiments, the method is carried out in a plurality of partitions (e.g., a multiwell plate). In some embodiments, subject p*MHC-I complexes are incubated with plurality of chaperones, dipeptides, multimer backbones, and different peptides of interest under conditions to form pMHC-I multimers in each of the partitions, wherein each partition includes a different peptide of interest. Thus, each partition is used produced pMHC-I multimers that include a different peptide of interest. In some embodiments, the resulting pMHC-I multimers (e.g., tetramers) are subsequently pooled to form the pMHC-I multimer library.

In some embodiments, each of the pMHC-I multimers in the library have the same MHC class I allele. In certain embodiments, the MHC class I is HLA-A. In an exemplary embodiment, the HLA-A is HLA-A02. In other embodiments, the pMHC-I multimer in the library include H-2 MHC class I. In exemplary embodiments, the H-2 is H-2Dd or H-2Ld.

In some embodiments, the library includes pMHC-I multimers with different MHC class I alleles. In some embodiments, the library includes pMHC-I tetramers.

In certain embodiments, the pMHC-I multimer library includes over 10, 20, 30, 40, 50, 60, 70, 80, 90, 100, 200, 250, 300, 400, 500, 600, 700, 800, 900, 1,000, 1×104, 1×105, 1×106, 1×107, or 1×108 different peptides. In some embodiments, each pMHC-I multimer in the library includes a detectable marker. In some embodiments, each pMHC-I multimer in the library includes a nucleic acid bar code or a fluorophore that is used to identify peptide of interest included in the pMHC-I multimer, wherein each barcode or fluorophore corresponds to a different peptide of interest. In some embodiments, each pMHC-I multimer in the library includes the same detectable label.

Methods of Use

In certain embodiments, the pMHC-I multimer is a pMHC-I tetramer. The pMHC-I tetramers provided herein can be used to study pathogen immunity, for the development of vaccines, in the evaluation of antitumor response, in allergy monitoring and desensitization studies, and in autoimmunity. See, e.g., Nepom et al., *J Immunol* 188 (6) 2477-2482 (2012); and Davis et al., *Nature Reviews Immunology* 11:551-558 (2011).

In some embodiments, the pMHC-I multimers are used to characterize T cell (e.g., CD8 T cell) responses to a vaccine, including, but not limited to influenza, yellow fever, tuberculosis, coronavirus (e.g. SARS-CoV2), and HIV/SIV vaccines. In an exemplary embodiment, the vaccine is a cancer vaccine in other embodiments, the vaccine is a viral vaccine. In particular embodiments, the cancer vaccine is melanoma or chronic myeloid leukemia. In such embodiments, a sample (e.g., a blood sample) of a vaccinated patient is contacted with one or more of the pMHC-I multimers that include one or more peptide of interests derived from the vaccine to identify and monitor antigen specific T cells that are produced in response to the vaccine.

In other embodiments, the pMHC-I multimers are used to characterize past exposure to a pathogen, such as SARS-CoV-2. In such embodiments, a blood sample of a subject is contacted with one or more of the disclosed pMHC-I multimers that include one or more of the disclosed SARS-CoV-2 peptides disclosed herein. The number of antigen specific T cells in the subject can be used to determine whether or not the subject was previously exposed to SARS-CoV-2.

The pMHC-I multimers provided herein can also be used to isolate and enrich particular antigen specific T cells for therapeutic use. See, e.g., Cobbold et al., *J. Exp. Med.* 202:379-386 (2006); and Davis et al., *Nature Reviews Immunology* 11:551-558 (2011). In this particular application, patient samples are contacted with sortable pMHC-I multimers that include a peptide antigen of interest and a label that allows for sorting (e.g., a fluorophore or nucleic acid label). Antigen specific T cells that bind the pMHC-I multimer are subsequently isolated and purified, for example, using flow cytometry or similar cell sorting and identification techniques.

In certain embodiments, the pMHC-I multimers provided herein are used for epitope mapping. In this method, a plurality of pMHC-I multimers that include different peptides derived from an antigen of interest (e.g., a tumor antigen or a viral antigen) are contacted with a sample from a subject. Antigen specific T cells are detected and the corresponding epitope peptide sequences are identified any technique known in the art, include, for example, flow cytometry and cell sorting techniques. See, e.g., Bentzen et al., *Nat Biotechnol.* 34(10):1037-1045 (2016).

In some embodiments, the pMHC-I multimers provided herein are used to determine a T cell profile of one or more subjects. In such an embodiment, a sample from a subject is contacted with a library of pMHC-I multimers that include a library of peptide of interest and a detectable label. Identification of antigen specific T cells that bind particular peptides of interest presented in the context of the pMHC-I multimers is achieved using the detectable label. The methods described herein allow for the large scale production of pMHC-I multimer libraries that can in turn be used for high throughput T cell profiling.

In another aspect, the pMHC-I multimers can be used therapeutically for the targeted elimination of particular antigen specific T cells in a subject. In one embodiment, the pMHC-I multimers are conjugated to a cytotoxic agent or a toxin. When administered to a subject, the pMHC-I multimer conjugates attach to and facilitate the elimination of particular antigen specific T cells.

The disclosed pMHC-I multimers can be tracked and detected using any suitable techniques including, but not limited to, techniques utilizing detectable labels and nucleic acid barcodes that allow identification of particular peptide-MHC class I multimers. In addition, T cells of interest isolated in such methods can also be identified using similar techniques.

T cells of interest that interact with pMHC-I multimers can be isolated using any suitable technique including, for example, flow cytometry techniques. Isolated T cells and corresponding peptide-MHC class I multimers can then be characterized using any suitable method, for example, the ECCITE-seq method as described in Mimitou E P et al, Nature Methods 16, 409-412 (2019) (incorporated by reference herein) in conjunction with the Chromium Single Cell Immune Profiling Solution with Feature Barcode Technology (10× Genomics). This method incorporates a cellular barcode into cDNA generated from both tetramer oligos and TCR mRNA, thus the pairing of cellular barcodes can connect TCR sequences and other mRNAs with pMHC-I multimers specificities.

EXPERIMENTAL SECTION

Example 1—Loading High Affinity Peptides Using Catalytic Amounts of TAPBPR

To evaluate whether exchange of placeholder peptides for high affinity peptides can occur when TAPBPR is provided at catalytic concentrations, a native gel electrophoresis assay was used. This allowed for the monitoring of the formation of different pMHC species upon overnight incubation in the presence of 10-fold molar excess of different peptides and varying molar ratios of TAPBPR (FIG. 1). Under these conditions, complete peptide exchange on gTAX/HLA-A*02:01 was obtained using a molar ratio as low as 1:1000 TAPBPR: MHC, while no exchange was observed for a non-specific peptide, or in the absence of TAPBPR. In this assay the electrophoretic mobility of different p*MHC molecules is dependent on the net charge of the bound peptide, which allowed for the resolving of distinct protein bands of HLA-A*02:01 loaded with peptides of disparate charges from −2 to +1 in overnight catalytic peptide exchange reactions (FIG. 2). Taken together, these results highlight the use of TAPBPR as a peptide exchange catalyst, which can be advantageous for high throughput applications.

Methods

All peptide sequences are provided in standard single letter code. Peptides used for MHC refoldings and production of the neoepitope library were purchased from Genscript® at 98% purity or as pepsets from Mimotopes as crude peptides and dissolved in 8.25% Acetonitrile, 25% DMSO, and 66.75% $H_2O$. Peptide binding affinities were predicted using netMHCpan 4.0 (Jurtz et al., *J. Immunol.* 199:3360-3368 (2017)).

In vitro refolding of p*MHC molecules: Plasmid DNA encoding the luminal domain of class I MHC (MHC-I) heavy chain HLA-A*02:01 and human β2-microglobulin (hβ2m,) were provided by the tetramer facility (Emory University), and transformed into *Escherichia coli* BL21 (DE3) (Novagen). MHC-I proteins were expressed in Luria-Broth media, and inclusion bodies (IBs) were purified using standard protocols (Garboczi et al., Proc. Natl Acad. Sci. USA 89:3429-3433 (1992)). In vitro refolding of pMHC-I molecules was performed by slowly diluting a 200 mg mixture of MHC-I and hβ2m at a 1:3 molar ratio over 24 hours in refolding buffer (0.4 M L-Arginine, 100 mM Tris pH 8, 2 mM EDTA, 4.9 mM reduced glutathione, 0.57 mM oxidized glutathione) containing 10 mg of synthetic peptide purchased from Genscript® at 98% purity at 4° C. HLA-A*02:01 was refolded with variants of LLFGYPVYV (SEQ ID NO:1) (TAX) derived from HTLV-1 including _LFGYPVYV (SEQ ID NO: 40) (gTAX), N-terminally acetylated TAX (Ac-LLFGYPVYV) (SEQ ID NO:2), ILFGYPVYV (SEQ ID NO: 3) where the first residue is a D-leucine or with ELAGIGILTV (SEQ ID NO: 38) (MART-1) derived from Melan-A.

Recombinant TAPBPR expression and purification: The luminal domain of TAPBPR was expressed using a stable *Drosophila* S2 cell line (described in Morozov et al, supra) induced with 1 mM $CuSO_4$ for 4 days and purified using affinity-based and size exclusion chromatography (Jiang, J. et al, *Science* 358, 1064-1068 (2017), incorporated by reference herein). Briefly, $His_6$-tagged TAPBPR was captured from the supernatant by affinity chromatography using high-density metal affinity agarose resin (ABT, Madrid). Eluted TAPBPR was further purified by size exclusion using a Superdex 200 10/300 increase column at a flow rate of 0.5 ml/min in 100 mM NaCl and 20 mM sodium phosphate pH 7.2.

Native gel electrophoresis: Peptide-deficient MHC-I/TAPBPR complexes were incubated with the indicated molar ratio of relevant (TAX) or irrelevant (P18-I10) peptide for 1 h at room temperature. Samples were run at 90 V on 8% polyacrylamide gels in 25 mM TRIS pH 8.8, 192 mM glycine, at 4° C. for 4.5 hours and developed using InstantBlue (Expedeon).

Example 2—Rapid MHC-I Binding Assessment and High Throughput Multimer Production of SARS-CoV-2 Epitopic Peptides As a primary step in the immune surveillance of virus-infected cells, cytotoxic CD8 T cells recognize immunogenic peptides bound to MHC-I molecules. While multitudinous SARS-CoV-2 CD8 and CD4 T cell epitopes have been predicted using computational approaches, further experimental characterization of peptide binding and antigen-specific responses in patients are required for actionable value in the development of diagnostic and therapeutic tools. Here, a library of pMHC-I complexes comprising a panel of predicted SARS-CoV-2 T cell epitopes was generated for rapid assessment of their assembly. Disclosed herein is a protocol using the MHC-I peptide editor TAPBPR to promote exchange of placeholder peptide for high-affinity SARS-CoV-2 peptides to yield pMHC molecules. 20 peptides derived from SARS-CoV-2 increase the melting temperature of pMHC-I by at least 5° C. to a maximum of 21° C., relative to the placeholder peptide, suggesting tight capture in the MHC-I peptide-binding groove. The disclosed approach allows for rapid selection of potentially immunogenic peptides and high throughput production of SARS-CoV-2 pMHC-I multimers as a tool to monitor T cell responses in patients, and to identify high-affinity, immunogenic peptides for vaccine development.

Cytotoxic CD8+ T cells recognize foreign or aberrant antigens that are presented by class I major histocompatibility complex (MHC-I, in human known as HLA-A, -B, -C) through T cell receptors (TCRs) as a critical step to trigger the adaptive immune responses against virus (12). MHC-I proteins selectively display a diverse antigenic peptide pool of 8 to 15 amino acids on the cell surface, providing a way to perform immune surveillance of cancers and viral infections (13,14). It has been shown that 15-mer SARS-CoV-2 epitopic peptides derived from the spike, nucleocapsid, and membrane proteins with 11-amino-acid-overlap bound to MHC-I and MHC-II could activate virus-specific T cells (15). Both SARS-CoV-2 spike protein-reactive CD4+ and CD8+ T cells have recently been detected among COVID-19 patients (16,17). Previous studies of SARS-COV have revealed a greater magnitude and a longer duration of virus-specific CD8+ relative to CD4+ T cells (18-20). Therefore, detailed knowledge of SARS-CoV-2 immunodominant epitopes presented by MHC-I is a prerequisite to quantify and monitor antigen-specific T cell responses. To date, many computational methods have been developed to predict T cell epitopes, including machine learning and bioinformatic approaches (21) that rely on the available data set from Immune Epitope Database (22), and structure-based approaches that model the bound peptide conformation de novo (23). Structure-guided modeling of SARS-CoV-2 T cell epitopes using the program Rosetta has identified peptides that potentially bind to the common human allele HLA-A*02:01 (24). While in-silico methods can rapidly identify promising epitopic peptide candidates, their results must be further experimental validated for MHC-I binding and immunogenicity in a clinical setting.

Due to the instability of empty (peptide-deficient) MHC-I molecules, epitopic peptides are often loaded in individual refolding reactions (25), rendering the process of generating properly conformed SARS-CoV-2 pMHC-I molecules tedious, and time-consuming. Conditional ligands used to stabilize empty MHC-I can be removed by UV exposure (26) or temperature elevation (27) to promote the loading of desired peptides. However, the use of cleavable peptides requires a more elaborate protein purification protocol, leading to protein aggregation and sample loss during the peptide exchange step. A robust method (28) using the molecular chaperone TAP-Binding Protein Related (TAPBPR) to generate fluorescently-tagged, pMHC-I multimers using in vitro peptide exchange (29,30) has been disclosed. Here, this method is used to generate pMHC-I molecules encompassing previously predicted SARS-CoV-2 epitopic peptides, bound to HLA-A*02:01 (24). 32 SARS-CoV-2 epitopic peptides were rapidly assessed for their binding on HLA-A*02:01 through a differential scanning fluorimetry (DSF) assay (31). pMHC-I complexes with confirmed peptide loading were selected for multimerization with fluorophore-labeled streptavidin or Klickmer®. As DSF integration allows a facile experimental search for strong binders from a wide range of predicted SARS-CoV-2 epitopes, TAPBPR-mediated peptide exchange makes high throughput SARS-CoV-2 pMHC multimer production feasible, and scalable.

Materials

SARS-CoV-2 epitopic peptides. All peptide sequences are given as standard single letter code. A total of 32 SARS-CoV-2 epitopic peptides were selected using prediction by netMHCpan4.0 and RosettaMHC (24) and were purchased from Genscript® at a purity of >90%. The placeholder peptide gTAX was also purchased from Genscript® at a purity of 98%. Peptides were solubilized in distilled water at a 1 mM concentration, or in DMSO at a 20 mM concentration and dilute to 1 mM with distilled water.

Biotinylated pMHC-I/gTAX molecules. Plasmid DNA encoding the BirA tagged luminal domain of MHC-I heavy chains HLA-A*02:01 and human $\beta_2$-microglobulin (h$\beta_2$m) were provided by the NIH tetramer facility (Emory University) and transformed into *Escherichia coli* BL21 (DE3) cells (Novagen). BirA-tagged MHC-I proteins were expressed in Luria-Broth media, and inclusion bodies were collected and purified using a standard protocol (25). In vitro refolding of BirA-tagged pMHC-I molecules was performed by slowly diluting a 200 mg of BirA-tagged MHC-I and h$\beta_2$m at 1:3 molar ratio over 24 hours in a refolding buffer (0.4 M L-Arginine, 100 mM Tris pH 8, 2 mM EDTA, 4.9 mM reduced glutathione, 0.57 mM oxidized glutathione) containing 10 mg of the placeholder peptide gTAX. BirA-tagged pMHC-I/gTAX (p*MHC-I) refolding was proceeded for 96 hours and followed by size-exclusion chromatography (SEC) for protein purification.

BirA-tagged pMHC-I/gTAX molecules were then biotinylated using the BirA biotin-protein ligase bulk reaction kit (Avidity), according to the manufacturer's instructions. Biotinylated p*MHC-I was buffer exchanged into PBS pH 7.4 using Amicon® Ultra centrifugal filter units with a 10 kDa membrane cut-off, and the level of biotinylation was evaluated by SDS-PAGE gel shift assay in the presence of excess streptavidin. A biotinylated p*MHC-I (gTAX/HLA-A*02:01) solution at a final concentration of 5 mg/mL was obtained.

Recombinant TAPBPR. The luminal domain of TAPBPR was expressed using a stable *Drosophila* S2 cell line (provided by Dr. Kannan Natarajan, National Institute of Health) induced with 1 mM $CuSO_4$ for 4 days The recombinant TAPBPR-His tagged proteins were purified using nickel affinity and size exclusion chromatography (32). TAPBPR solutions at a final concentration of 12 UM and 120 μM were used.

Tetramers and Multimers. Streptavidin-R-Phycoerythrin (Streptavidin-PE) and Streptavidin-Allophycocyanin (Streptavidin-APC) conjugates were purchased from Prozyme® at a streptavidin concentration of 0.43 and 0.82 mg/mL. Klickmer-APC®, a streptavidin multimer conjugate label with APC at a stock concentration of 160 nM, was purchased from IMMUDEX.

Methods

SARS-CoV-2 pMHC-I multimer preparation. pMHC-I/gTAX (p*MHC-I) molecules were mixed with TAPBPR (10:1 p*MHC-I/TAPBPR molar ratio) and SARS-CoV-2 epitopic peptide (1:10 p*MHC-I/SARS-CoV-2 epitopic peptide molar ratio). Each reaction was incubated 1 hour at room temperature. After the exchange, the resulting SARS-CoV-2 pMHC-I molecules were ready to use in native gel electrophoresis and differential scanning fluorimetry.

Streptavidin-PE/APC (2:1 pMHC-I/streptavidin molar ratio) or Klickmer-APC® (IMMUDEX) (30:1 pMHC-I/streptavidin molar ratio) were added to SARS-CoV-2 pMHC-I molecules and incubated for one hour at 4° C. After the incubation, SARS-CoV-2 pMHC-I multimers were washed on a 96-well filter plate (AcroPrep™) with 1000 volumes of PBS to remove TAPBPR and excess peptide by centrifugation using Beckman Allegra 15R benchtop centrifuge and Beckman SX4750 swing-bucket rotor at 500 g for five minutes each time. A 96-well non-binding surface microplate (Corning®) was used to collect the flow-through. Biotinylated DNA barcodes (2:1 DNA oligos/streptavidin molar ratio, IDT) can be loaded, forming barcoded pMHC-I multimers using the previously illustrated protocol (28). Purified pMHC-I multimers can then be stored at 4° C. for up to 3 weeks for fluorescence-activated T cell sorting.

Alternatively, SARS-CoV-2 pMHC-I multimers can be generated directly by mixing individual SARS-CoV-2 peptide, pMHC-I/gTAX (p*MHC-I), TAPBPR, and Streptavidin-PE/APC at a molar ratio of 100:10:1:5 or Klickmer-APC® at a molar ratio of 300:30:3:1 and incubating for one hour at room temperature, followed by the previously mentioned purification by centrifugation step.

Native gel electrophoresis. pMHC-I/gTAX were exchanged for SARS-CoV-2 epitopic peptides 4, 10, 13, 8, 2, 7, 11, and 1 (Sequence: NLNESLIDL (SEQ ID NO:8) (P4), ILLLDQALV (P10), KLPDDFTGCV (SEQ ID NO:17) (P13), GMSRIGMEV (SEQ ID NO:12) (P8), VLNDILSRL (SEQ ID NO:6) (P2), LLLDRLNQL (SEQ ID NO:11) (P7), SLPGVFCGV (SEQ ID NO:15) (P11)), an irrelevant high-affinity peptide MART-1 (Sequence: ELAGIGILTV (SEQ ID NO: 38)), and a non-specific peptide, (NIH, Sequence: YPNVNIHNF (SEQ ID NO:41)) with the previously indicated molar ratio. Samples were run at 90 V on 12% polyacrylamide gels using a running buffer of 25 mM TRIS pH 8.5, 192 mM glycine at 4° C. for 5 hours, and developed using InstantBlue® (Expedeon®).

Differential scanning fluorimetry. Differential scanning fluorimetry measures the thermal stabilities of the SARS-CoV-2 pMHC-I molecules. 7 UM of SARS-CoV-2 pMHC-I were mixed with 10× Sypro Orange dye in a buffer of 50 mM NaCl, 20 mM sodium phosphate pH 7.2 to a final volume of 50 μL. Samples were loaded into MicroAmp® Fast 96 well plate and ran in triplicates. The experiment was performed on an Applied Biosystems ViiA 7 qPCR machine with excitation and emission wavelength set to 470 nm and 569 nm. The thermal stability was measured by gradually increasing temperature at a rate of 1° C. per minute between 25° C. to 95° C. Melting temperatures ($T_m$) were calculated in GraphPad Prism 7® by plotting the first derivative of each melting curve and taking the peak as the $T_m$. Errors in Table 1 represent the standard deviation of the $T_m$ in 3 replicates, individually analyzed.

Results and Discussion

A streamlined workflow of translating SARS-CoV-2 epitopic peptide predictions into pMHC-I molecules is outlined in FIG. 1. This high-throughput platform to generate a multimer library encompassing 32 computationally identified SARS-CoV-2 peptides predicted to bind to HLA-A*02:01 (24). HLA-A*02:01 is among the most prevalent alleles in the human population, presenting a wide range of immunodominant viral and tumor epitopes, which renders it a highly relevant system to understand MHC-I-restricted SARS-CoV-2-specific T cell responses (33,34). HLA-A*02:01 was refolded in the presence of gTAX (LFGYPVYV) (SEQ ID NO:40), an N-terminal truncated variant of the LLFGYPVYV (SEQ ID NO: 1) (TAX) peptide, which serves as a placeholder peptide (gTAX refolds with HLA-A2 successfully, but has significantly lower affinity than the full-length TAX peptide) (28,29). High-affinity SARS-CoV-2 epitopic peptides displace gTAX in the MHC-I groove in the presence of the molecular chaperone TAPBPR, which serves as a peptide exchange catalyst (28). Complete peptide exchange to form SARS-CoV-2 pMHC-I species can be obtained using a 1:10 TAPBPR: pMHC-I molar ratio, both under one-hour incubation at room temperature or overnight incubation at 4° C. (28). Detection of stable SARS-CoV-2 pMHC-I complexes and further ranking of the peptides can be performed using a differential scanning fluorimetry (DSF) assay (31), which has minimal requirements in protein sample concentration and can be performed at high throughput. The measured DSF thermal stability ($T_m$) values were shown to correlate with predicted $IC_{50}$ values, and more recently with detailed dissociation constants from ITC experiments (35), for A02-restricted peptides.

Finally, stable SARS-CoV-2 pMHC-I molecules are selected and loaded onto fluorophore-labeled streptavidin or Klickmers®, which can be readily used to stain peripheral blood mononuclear cells (PBMCs) to detect antigen-specific CD8 T cells.

Rapid Assessment of SARS-CoV-2 p/MHC-I Binding

The binding of predicted SARS-CoV-2 epitopes to MHC-I was first monitored using a native gel electrophoretic mobility shift assay through the appearance of distinct protein bands according to the charge and hydrodynamic radius of the resulting pMHC molecules (FIG. 4A). p*MHC-I/gTAX was exchanged for SARS-CoV-2 peptides 4, 10, 13, 8, 2, 7, 11, and 1 or MART-1, a known high-affinity peptide. Increasing net charges of tightly bound SARS-CoV-2 peptides led to ascending band positions. In contrast, p*MHC-I/gTAX incubated with a non-specific peptide showed no condensed band, which is similar to MHC-I refolded with gTAX, likely due to low-affinity peptide loss and protein precipitation under the conditions of the gel (28). Although native gel electrophoresis monitors the formation of exchanged pMHC-I molecules, running it on a large number of samples can be time-consuming and provide no quantitative analysis on pMHC-I stability and binding affinity. Therefore, differential scanning fluorimetry (DSF) (31) was used to detect the formation of stable pMHC-I upon the loading of each SARS-CoV-2 peptide.

MHC-I refolded with gTAX gave the lowest $T_m$ value at 40° C., consistent with previously reported results (28,31). Overlaid DSF temperature profile of exchanged pMHC-I/MART-1, SARS-CoV-2 epitopic peptides 3, 2, 10, and 11 show increasing thermal stabilities with ascending $T_m$ values from 46° C. to 59° C. (FIGS. 4B and 4C)). Increased $T_m$ values represent enhanced thermal stabilities, which can correlate with improved peptide affinity (31). A total of 32 SARS-CoV-2 epitopic peptides and high-affinity MART-I and CMV NV9 peptide, used as controls, were prepared into pMHC-I through TAPBPR-mediated peptide exchange while individually refolded HLA-A*02:01/gTAX and MART-1 were used as negative and positive controls, respectively. 20 out of 32 computational identified epitopic peptides show an increase in $T_m$ by more than 5° C. compared to HLA-A*02:01/gTAX (Table 1). These apparent $T_m$ values were considered as an additional indication of tight MHC-I binders from our initial set of predicted T cell epitopes. Furthermore, incorporating DSF in 96-well format offers a rapid method of confirming peptide loading, thereby accelerating the production of SARS-CoV-2 pMHC-I multimers.

SARS-CoV-2 pMHC-I multimers were generated by mixing SARS-CoV-2 peptide, gTAX/MHC-I (HLA-A*02:01), TAPBPR, and fluorescent-labeled streptavidin or Klickmer® directly on a 96-well plate (FIG. 3 and FIG. 5A). TAPBPR enhances the efficiency of peptide exchange in vitro by mimicking the cellular pathway of antigen processing for MHC-I molecules to load immunodominant peptides (12). High-affinity peptides among predicted SARS-CoV-2 epitopes bind to MHC-I/TAPBPR, leading to TAPBPR dissociation to form multimers (FIG. 5A), (28,29)). After the reaction, excess peptides and TAPBPR were removed by centrifugation on a 96-well filter plate with a filter membrane cut-off of 100 kDa (FIG. 4B). Because TAPBPR promotes the release of high-affinity peptides from the MHC binding groove in vitro (29), TAPBPR-mediated peptide exchange might leave some empty MHC-I, thereby reducing the staining efficiency of the resulting multimers. To resolve this issue, TAPBPR was added catalytically at 1:10 molar ratio, and free TAPBPR molecules were removed using centrifugation upon completion of the peptide exchange reaction.

TABLE 1

Binding data for SARS-CoV-2 epitopic peptides.

| Peptide Index | Peptide Sequence | $T_m$ (° C.) |
|---|---|---|
| 1 | ALNTLVKQL (SEQ ID NO: 5) | 48.3 ± 0.6 |
| 2 | VLNDILSRL (SEQ ID NO: 6) | 50.3 ± 0.0 |
| 3 | RLNEVAKNL (SEQ ID NO: 7) | 46.3 ± 0.6 |
| 4 | NLNESLIDL (SEQ ID NO: 8) | 47.3 ± 0.6 |
| 5* | FIAGLIAIV (SEQ ID NO: 9) | 48.3 ± 0.6 |
| 6* | GLMWLSYFI (SEQ ID NO: 10) | 41.4 ± 7.9 |
| 7 | LLLDRLNQL (SEQ ID NO: 11) | 54.3 ± 0.6 |
| 8 | GMSRIGMEV (SEQ ID NO: 12) | 48.3 ± 0.0 |
| 9* | WLMWLIINL (SEQ ID NO: 13) | 42.4 ± 4.0 |
| 10 | ILLLDQALV (SEQ ID NO: 14) | 52.3 ± 0.0 |
| 11 | SLPGVFCGV (SEQ ID NO: 15) | 59.3 ± 0.0 |
| 12* | TLACFVLAAV (SEQ ID NO: 16) | 53.3 ± 0.6 |
| 13 | KLPDDFTGCV (SEQ ID NO: 17) | 53.3 ± 0.0 |
| 14* | SIIAYTMSL (SEQ ID NO: 18) | 53.3 ± 0.6 |
| 15* | TLMNVLTLV (SEQ ID NO: 19) | 61.2 ± 0.6 |
| 16 | ILLNKHIDA (SEQ ID NO: 20) | 43.4 ± 0.0 |
| 17 | VVFLHVTYV (SEQ ID NO: 21) | 52.3 ± 0.0 |
| 18 | RLDKVEAEV (SEQ ID NO: 22) | 51.3 ± 0.6 |
| 19 | RLQSLQTYV (SEQ ID NO: 23) | 61.2 ± 0.6 |
| 20 | AQFAPSASA (SEQ ID NO: 24) | 40.4 ± 1.1 |
| 21 | VLQLPQGTTL (SEQ ID NO: 25) | 39.4 ± 0.0 |
| 22 | LLLLDRLNQL (SEQ ID NO: 26) | 42.4 ± 0.6 |
| 23* | GLIAIVMVTI (SEQ ID NO: 27) | 40.4 ± 0.6 |
| 24 | IITTDNTFV (SEQ ID NO: 28) | 42.4 ± 0.6 |
| 25 | SMWALIISV (SEQ ID NO: 29) | 52.3 ± 0.6 |
| 26 | ALNTPKDHI (SEQ ID NO: 30) | 44.4 ± 0.6 |
| 27* | LALLLLDRL (SEQ ID NO: 31) | 43.3 ± 1.5 |
| 28 | LQLPQGTTL (SEQ ID NO: 32) | 44.4 ± 1.1 |
| 29 | LITGRLQSL (SEQ ID NO: 33) | 44.4 ± 0.6 |
| 30 | FPRGQGVPI (SEQ ID NO: 34) | 45.4 ± 1.5 |
| 31* | LLLQYGSFC (SEQ ID NO: 35) | 47.3 ± 0.6 |
| 32 | TTLPKGFYA (SEQ ID NO: 36) | 46.3 ± 0.6 |
| CMV NV9 | NLVPMVATV (SEQ ID NO: 37) | 51.3 ± 0.0 |
| MART-1 | ELAGIGILTV (SEQ ID NO: 38) | 54.3 ± 0.6 |
| MART-1 Refolded | ELAGIGILTV (SEQ ID NO: 39) | 56.4 ± 0.0 |
| gTAX Refolded | LFGYPVYV (SEQ ID NO: 40) | 40.4 ± 0.6 |

DSF thermal stability assays were performed on a 96-well plate for p/HLA-A*02:01 complexes prepared for 32 epitopic peptides predicted from SARS-CoV-2, and 2 confirmed high-affinity epitopic peptides (CMV pp65 and MART-1), used as positive controls. pHLA complexes corresponding to the 32 SARS-CoV-2, MART-1 and CMV NV9 peptides were prepared by TAPBPR-mediated peptide exchange. A 10-fold molar excess of the free peptide was used to promote exchange during an overnight incubation at 4° C. MART-1 and gTAX were also produced by conventional refolding. The DSF temperature profiles were analyzed, and $T_m$ values were extracted by taking the first derivative (maximum slope of the DSF temperature curve). Errors represent the standard deviation of 3 replicates, individually analyzed. Peptides colored in gray were selected for the dextramer library production. Peptides denoted with an asterisk were solubilized using 0.4% DMSO in PBS buffer. Peptides highlighted in shaded color showed $T_m$ values greater than 45° C., indicating tight peptide binding, and were included in our dextramer library.

REFERENCES

The following publications are referenced in the text of Example 2 and are incorporated by reference herein in their entireties.

12. Germain R N, Margulies D H. The biochemistry and cell biology of antigen processing 12. and presentation. Annu Rev Immunol (1993) 11:403-450. doi:10.1146/annurev.iy.11.040193.002155
13. Kaufman J. Unfinished Business: Evolution of the MHC and the Adaptive Immune System of Jawed Vertebrates. Annu Rev Immunol (2018) doi:10.1146/annurev-immunol-051116-052450
14. Rock K L, Reits E, Neefjes J. Present Yourself! By MHC Class I and MHC Class II Molecules. Trends Immunol (2016) 37:724-737. doi:10.1016/j.it.2016.08.010
15. Leung W, Soh T G, Linn Y C, Low J G-H, Loh J, Chan M, Chng W J, Koh L P, Poon M L-M, Ng K P, et al. SUCCESSFUL MANUFACTURING OF CLINICAL-GRADE SARS-CoV-2 SPECIFIC T CELLS FOR ADOPTIVE CELL THERAPY. Infectious Diseases (except HIV/AIDS) (2020). doi:10.1101/2020.04.24.20077487
16. Braun J, Loyal L, Frentsch M, Wendisch D, Georg P, Kurth F, Hippenstiel S, Dingeldey M, Kruse B, Fauchere F, et al. Presence of SARS-CoV-2 reactive T cells in COVID-19 patients and healthy donors. medRxiv (2020) 2020.04.17.20061440. doi:10.1101/2020.04.17.20061440
17. Chour W, Xu A M, Ng A H C, Choi J, Xie J, Yuan D, Lee J K, Delucia D C, Edmark R, Jones L, et al. Shared Antigen-specific CD8+ T cell Responses Against the SARS-CoV-2 Spike Protein in HLA A*02:01 COVID-19 Participants. Infectious Diseases (except HIV/AIDS) (2020). doi:10.1101/2020.05.04.20085779
18. Li C K, Wu H, Yan H, Ma S, Wang L, Zhang M, Tang X, Temperton N J, Weiss R A, Brenchley J M, et al. T Cell Responses to Whole SARS Coronavirus in Humans. J Immunol Baltim Md 1950 (2008) 181:5490-5500.
19. Yang L-T, Peng H, Zhu Z-L, Li G, Huang Z-T, Zhao Z-X, Koup R A, Bailer R T, Wu C-Y. Long-lived effector/central memory T-cell responses to severe acute respiratory syndrome coronavirus (SARS-COV) S antigen in recovered SARS patients. Clin Immunol Orlando Fla (2006) 120:171-178. doi:10.1016/j.clim.2006.05.002
20. Peng H, Yang L, Wang L, Li J, Huang J, Lu Z, Koup R A, Bailer R T, Wu C. Long-lived memory T lymphocyte responses against SARS coronavirus nucleocapsid protein in SARS-recovered patients. Virology (2006) 351:466-475. doi:10.1016/j.virol.2006.03.036
21. Grifoni A, Sidney J, Zhang Y, Scheuermann R H, Peters B, Sette A. A Sequence Homology and Bioinformatic Approach Can Predict Candidate Targets for Immune Responses to SARS-CoV-2. Cell Host Microbe (2020) 27:671-680.e2. doi:10.1016/j.chom.2020.03.002
22. Vita R, Mahajan S, Overton J A, Dhanda S K, Martini S, Cantrell J R, Wheeler D K, Sette A, Peters B. The Immune Epitope Database (IEDB): 2018 update. Nucleic Acids Res (2019) 47:D339-D343. doi:10.1093/nar/gky1006
23. Antunes* D A, Abella J R, Devaurs D, Kavraki* M M R and L E. Structure-based Methods for Binding Mode and Binding Affinity Prediction for Peptide-MHC Complexes. Curr Top Med Chem (2018) 18:2239-2255.
24. Nerli S, Sgourakis N G. Structure-based modeling of SARS-CoV-2 peptide/HLA-A02 antigens. bioRxiv (2020) 2020.03.23.004176. doi:10.1101/2020.03.23.004176
25. Garboczi D N, Hung D T, Wiley D C. HLA-A2-peptide complexes: Refolding and crystallization of molecules expressed in *Escherichia coli* and complexed with single antigenic peptides. Proc Natl Acad Sci USA, (1992) 89:3429-3433. doi: 10.1073/pnas.89.8.3429.
26. Bakker A H, Hoppes R, Linnemann C, Toebes M, Rodenko B, Berkers C R, Hadrup S R, Esch W J E van, Heemskerk M H M, Ovaa H, et al. Conditional MHC class I ligands and peptide exchange technology for the human MHC gene products HLA-A1, -A3, -A11, and -B7. Proc Natl Acad Sci (2008) 105:3825-3830. doi:10.1073/pnas.0709717105
27. Luimstra J J, Garstka M A, Roex M C J, Redeker A, Janssen G M C, van Veelen P A, Arens R, Falkenburg J H F, Neefjes J, Ovaa H. A flexible MHC class I multimer loading system for large-scale detection of antigen-specific T cells. J Exp Med (2018) 215:1493-1504. doi:10.1084/jem.20180156
28. Overall S A, Toor J S, Hao S, Yarmarkovich M, O'Rourke S M, Morozov G I, Nguyen S, Japp A S, Gonzalez N, Moschidi D, et al. High throughput pMHC-I tetramer library production using chaperone-mediated peptide exchange. Nat Commun (2020) 11:1-13. doi:10.1038/s41467-020-15710-1
29. McShan A C, Natarajan K, Kumirov V K, Flores-Solis D, Jiang J, Badstubner M, Toor J S, Bagshaw C R, Kovrigin E L, Margulies D H, et al. Peptide exchange on MHC-I by TAPBPR is driven by a negative allostery release cycle. Nat Chem Biol (2018) 14:811-820. doi:10.1038/s41589-018-0096-2
30. Morozov G I, Zhao H, Mage M G, Boyd L F, Jiang J, Dolan M A, Venna R, Norcross M A, McMurtrey C P, Hildebrand W, et al. Interaction of TAPBPR, a tapasin homolog, with MHC-I molecules promotes peptide editing. Proc Natl Acad Sci (2016) 113: E1006-E1015. doi:10.1073/pnas.1519894113
31. Hellman L M, Yin L, Wang Y, Blevins S J, Riley T P, Belden O S, Spear T T, Nishimura M I, Stern L J, Baker B M. Differential scanning fluorimetry based assessments of the thermal and kinetic stability of peptide-MHC complexes. J Immunol Methods (2016) 432:95-101. doi:10.1016/j.jim.2016.02.016
32. Jiang J, Natarajan K, Boyd L F, Morozov G I, Mage M G, Margulies D H. Crystal structure of a TAPBPR-MHC-I complex reveals the mechanism of peptide editing in antigen presentation. Science (2017) 358:1064-1068. doi:10.1126/science.aao5154

33. Chen K Y, Liu J, Ren E C. Structural and functional distinctiveness of HLA-A2 allelic variants. Immunol Res (2012) 53:182-190. doi:10.1007/s12026-012-8295-5
34. González-Galarza F F, Takeshita L Y C, Santos E J M, Kempson F, Maia M H T, Silva A L S da, Silva A L T e, Ghattaoraya G S, Alfirevic A, Jones A R, et al. Allele frequency net 2015 update: new features for HLA epitopes, KIR and disease and HLA adverse drug reaction associations. Nucleic Acids Res (2015) 43:D784-D788. doi:10.1093/nar/gku1166
35. McShan A C, Devlin C A, Morozov G I, Overall S A, Moschidi D, Akella N, Procko E, Sgourakis N G. TAPBPR Promotes Antigen Loading on MHC-I Molecules Using a Peptide Trap. bioRxiv (2020) 2020.04.24.059634. doi:10.1101/2020.04.24.059634
36. Martinez R J, Evavold B D. Lower Affinity T Cells are Critical Components and Active Participants of the Immune Response. Front Immunol (2015) 6: doi:10.3389/fimmu.2015.00468
37. Gimenez E, Albert E, Torres I, Remigia M J, Alcaraz M J, Galindo M J, Blasco M L, Solano C, Forner M J, Redon J, et al. SARS-CoV-2-reactive interferon-γ-producing CD8+ T cells in patients hospitalized with Coronavirus viral disease-2019. medRxiv (2020) 2020.05.18.20106245. doi:10.1101/2020.05.18.20106245
38. Batard P, Peterson D A, Devêvre E, Guillaume P, Cerottini J-C, Rimoldi D, Speiser D E, Winther L, Romero P. Dextramers: New generation of fluorescent MHC class I/peptide multimers for visualization of antigen-specific CD8+ T cells. J Immunol Methods (2006) 310:136-148. doi:10.1016/j.jim.2006.01.006

What is claimed is:

1. A method of making a plurality of peptide receptive MHC-I complexes each of which can accept a peptide of interest, each peptide receptive MHC-I complex comprising an MHC class I heavy chain and an β2-microglobulin, the method comprising:

a) incubating a plurality of MHC class I heavy chains, and a plurality of β2-microglobulins and a plurality of placeholder peptides under conditions wherein the MHC class I heavy chains, the β2-microglobulins and the placeholder peptides form a plurality of placeholder peptide-MHC class I (p*MHC-I) complexes, wherein the MHC Class I heavy chain is HLA-A*02:01 and the placeholder peptide is gTAX/HLAA* or AcLL-FGYPVYV (SEQ ID NO:2), wherein the MHC class I heavy chain is H-2D$^d$ and the placeholder peptide is gP18-I10 (GPGRAFVTI) (SEQ ID NO:4), or wherein the MHC class I heavy chain is H-2L$^d$ and the placeholder peptide is QL9 (QLSPFPFDL) (SEQ ID NO:42); and b) contacting the p*MHC-I complexes with a plurality of Tapasin Binding Protein Related (TAPBPR) chaperones, wherein the chaperones are provided at less than a 1:1 molar ratio of chaperone to p*MHC-I, thereby forming the plurality of peptide receptive MHC-I complexes.

2. The method of claim 1, wherein the p*MHC-I complexes are purified and biotinylated prior to the contacting with the chaperones.

3. The method of claim 1, wherein the molar ratio of chaperone to p*MHC-I is less than 1:2, less than 1:10, less than 1:50, less than 1:100, less than 1:500, or less than 1:1000.

4. A method of making a plurality of peptide-MHC class I (pMHC-I) complexes, each complex comprising an MHC Class I heavy chain, a β2-microglobulin, and a peptide of interest, the method comprising:

a) incubating a plurality of MHC class I heavy chains, a plurality of β2-microglobulins and a plurality of placeholder peptides under conditions wherein the plurality of MHC class I heavy chains, β2-microglobulins and placeholder peptides form a plurality of placeholder peptide-MHC class I (p*MHC-I) complexes, wherein the MHC Class I heavy chain is HLA-A*02:01 and the placeholder peptide is gTAX/HLAA* or AcLL-FGYPVYV (SEQ ID NO:2), wherein the MHC class I heavy chain is H-2D$^d$ and the placeholder peptide is gP18-I10 (GPGRAFVTI) (SEQ ID NO:4), or wherein the MHC class I heavy chain is H-2L$^d$ and the placeholder peptide is QL9 (QLSPFPFDL) (SEQ ID NO:42);

b) forming a plurality of peptide receptive MHC-I complexes by contacting the plurality of p*MHC-I complexes with a plurality of Tapasin Binding Protein Related (TAPBPR) chaperones, wherein the chaperones are provided at a molar ratio of chaperone to p*MHC-I complex of less than 1:1, thereby forming a plurality of peptide receptive MHC-I complexes; and c) contacting the plurality of peptide receptive MHC-I complexes with a plurality of peptides of interest, thereby forming the plurality of pMHC-I complexes.

5. The method of claim 4, wherein the p*MHC-I is purified and biotinylated prior to the contacting with the chaperones.

6. The method of claim 4, wherein the molar ratio of chaperone to p*MHC-I is less than 1:2, less than 1:10, less than 1:50, less than 1:100, less than 1:500, or less than 1:1000.

7. A method of making a plurality of peptide-MHC class I (pMHC-I) multimer complexes, each complex comprising an MHC class I multimer and a peptide of interest, the method comprising:

a) incubating a plurality of MHC class I heavy chains, a plurality of β2-microglobulins, and a plurality of placeholder peptides under conditions wherein the plurality of MHC class I heavy chains, β2-microglobulins and placeholder peptides form a plurality of placeholder peptide-MHC class I (p*MHC-I) complexes, wherein the MHC Class I heavy chain is HLA-A*02:01 and the placeholder peptide is gTAX/HLAA* or AcLL-FGYPVYV (SEQ ID NO:2), wherein the MHC class I heavy chain is H-2D$^d$ and the placeholder peptide is gP18-I10 (GPGRAFVTI) (SEQ ID NO:4), or wherein the MHC class I heavy chain is H-2L$^d$ and the placeholder peptide is QL9 (QLSPFPFDL) (SEQ ID NO:42);

b) contacting the plurality of p*MHC-I complexes with a plurality of Tapasin Binding Protein Related (TAPBPR) chaperones, wherein the chaperones are provided at a molar ratio of chaperone to p*MHC-I complex of less than 1:1, thereby forming a plurality of peptide receptive MHC-I complex;

c) attaching the plurality of peptide receptive MHC-I complexes to multimer backbones, thereby forming a plurality of peptide receptive MHC-I multimers; and d) contacting the plurality of peptide receptive MHC-I multimers with a plurality of peptides of interest, thereby forming a plurality of pMHC-I multimer complexes.

8. A method of making a plurality of peptide-MHC class I (pMHC-I) multimer complexes, each complex comprising an MHC class I multimer and a peptide of interest, the method comprising:

a) providing a plurality of placeholder peptide-MHC class I (p*MHC-I) complexes, wherein each p*MHC-I complex comprises an MHC class I heavy chain, an β2-microglobulin, and a placeholder peptide, wherein the MHC Class I heavy chain is HLA-A*02:01 and the placeholder peptide is gTAX/HLAA* or AcLL-FGYPVYV (SEQ ID NO:2), wherein the MHC class I heavy chain is H-2D$^d$ and the placeholder peptide is gP18-I10 (GPGRAFVTI) (SEQ ID NO: 4), or wherein the MHC class I heavy chain is H-2L$^d$ and the placeholder peptide is QL9 (QLSPFPFDL) (SEQ ID NO:42);

b) contacting the plurality of p*MHC-I complexes with a plurality of Tapasin Binding Protein Related (TAPBPR) chaperones, multimer backbones, and peptides of interest under conditions to form a plurality of peptide-MHC class I multimer complexes, wherein the chaperones are provided at a molar ratio of chaperone to p*MHC-I complex of less than 1:1, thereby forming a plurality of peptide-MHC class I multimer complexes; and c) recovering the plurality of peptide-MHC class I multimer complexes.

9. The method of claim 7 or 8, wherein the molar ratio of chaperone to p*MHC-I is less than 1:2, less than 1:10, less than 1:50, less than 1:100, less than 1:500, or less than 1:1000.

10. The method of claim 7 or 8, wherein each of the MHC multimer-peptide complexes is further attached to a barcode DNA oligo.

11. The method claim 7 or 8, wherein the multimer backbones are selected from streptavidin, avidin and dextran backbones.

12. The method claim 7 or 8, wherein the p*MHC-I complexes are biotinylated.

* * * * *

SEQUENCE LISTING

```
<160> NUMBER OF SEQ ID NOS: 46

<210> SEQ ID NO 1
<211> LENGTH: 9
<212> TYPE: PRT
<213> ORGANISM: Artificial Sequence
<220> FEATURE:
<223> OTHER INFORMATION: Synthetic polypeptide (HTLV-1 epitope TAX11-19)

<400> SEQUENCE: 1

Leu Leu Phe Gly Tyr Pro Val Tyr Val
1               5


<210> SEQ ID NO 2
<211> LENGTH: 9
<212> TYPE: PRT
<213> ORGANISM: Artificial Sequence
<220> FEATURE:
<223> OTHER INFORMATION: Synthetic Polypeptide (N-terminally acetylated
      TAX)
<220> FEATURE:
<221> NAME/KEY: MOD_RES
<222> LOCATION: (1)..(1)
<223> OTHER INFORMATION: Leu is acetylated leucine

<400> SEQUENCE: 2

Leu Leu Phe Gly Tyr Pro Val Tyr Val
1               5


<210> SEQ ID NO 3
<211> LENGTH: 9
<212> TYPE: PRT
<213> ORGANISM: Artificial Sequence
<220> FEATURE:
<223> OTHER INFORMATION: Syntheic polypeptide
<220> FEATURE:
<221> NAME/KEY: MOD_RES
<222> LOCATION: (1)..(1)
<223> OTHER INFORMATION: Leu is D-leucine

<400> SEQUENCE: 3

Leu Leu Phe Gly Tyr Pro Val Tyr Val
1               5


<210> SEQ ID NO 4
<211> LENGTH: 9
<212> TYPE: PRT
<213> ORGANISM: Artificial Sequence
<220> FEATURE:
<223> OTHER INFORMATION: Syntheitc polypeptide (gP18-I10)
```

<400> SEQUENCE: 4

Gly Pro Gly Arg Ala Phe Val Thr Ile
1 5

<210> SEQ ID NO 5
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 5

Ala Leu Asn Thr Leu Val Lys Gln Leu
1 5

<210> SEQ ID NO 6
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 6

Val Leu Asn Asp Ile Leu Ser Arg Leu
1 5

<210> SEQ ID NO 7
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 7

Arg Leu Asn Glu Val Ala Lys Asn Leu
1 5

<210> SEQ ID NO 8
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 8

Asn Leu Asn Glu Ser Leu Ile Asp Leu
1 5

<210> SEQ ID NO 9
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 9

Phe Ile Ala Gly Leu Ile Ala Ile Val
1 5

<210> SEQ ID NO 10
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 10

```
Gly Leu Met Trp Leu Ser Tyr Phe Ile
1               5


<210> SEQ ID NO 11
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 11

Leu Leu Leu Asp Arg Leu Asn Gln Leu
1               5


<210> SEQ ID NO 12
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 12

Gly Met Ser Arg Ile Gly Met Glu Val
1               5


<210> SEQ ID NO 13
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 13

Trp Leu Met Trp Leu Ile Ile Asn Leu
1               5


<210> SEQ ID NO 14
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 14

Ile Leu Leu Leu Asp Gln Ala Leu Val
1               5


<210> SEQ ID NO 15
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 15

Ser Leu Pro Gly Val Phe Cys Gly Val
1               5


<210> SEQ ID NO 16
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 16
```

Thr Leu Ala Cys Phe Val Leu Ala Ala Val
1 5 10

<210> SEQ ID NO 17
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 17

Lys Leu Pro Asp Asp Phe Thr Gly Cys Val
1 5 10

<210> SEQ ID NO 18
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 18

Ser Ile Ile Ala Tyr Thr Met Ser Leu
1 5

<210> SEQ ID NO 19
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 19

Thr Leu Met Asn Val Leu Thr Leu Val
1 5

<210> SEQ ID NO 20
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 20

Ile Leu Leu Asn Lys His Ile Asp Ala
1 5

<210> SEQ ID NO 21
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 21

Val Val Phe Leu His Val Thr Tyr Val
1 5

<210> SEQ ID NO 22
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 22

Arg Leu Asp Lys Val Glu Ala Glu Val 1 5

<210> SEQ ID NO 23
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 23

Arg Leu Gln Ser Leu Gln Thr Tyr Val
1 5

<210> SEQ ID NO 24
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 24

Ala Gln Phe Ala Pro Ser Ala Ser Ala
1 5

<210> SEQ ID NO 25
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 25

Val Leu Gln Leu Pro Gln Gly Thr Thr Leu
1 5 10

<210> SEQ ID NO 26
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 26

Leu Leu Leu Leu Asp Arg Leu Asn Gln Leu
1 5 10

<210> SEQ ID NO 27
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 27

Gly Leu Ile Ala Ile Val Met Val Thr Ile
1 5 10

<210> SEQ ID NO 28
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 28

Ile Ile Thr Thr Asp Asn Thr Phe Val
1 5

<210> SEQ ID NO 29
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 29

Ser Met Trp Ala Leu Ile Ile Ser Val
1 5

<210> SEQ ID NO 30
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 30

Ala Leu Asn Thr Pro Lys Asp His Ile
1 5

<210> SEQ ID NO 31
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 31

Leu Ala Leu Leu Leu Leu Asp Arg Leu
1 5

<210> SEQ ID NO 32
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 32

Leu Gln Leu Pro Gln Gly Thr Thr Leu
1 5

<210> SEQ ID NO 33
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 33

Leu Ile Thr Gly Arg Leu Gln Ser Leu
1 5

<210> SEQ ID NO 34
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 34

Phe Pro Arg Gly Gln Gly Val Pro Ile
1 5

<210> SEQ ID NO 35
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 35

Leu Leu Leu Gln Tyr Gly Ser Phe Cys
1               5

<210> SEQ ID NO 36
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 36

Thr Thr Leu Pro Lys Gly Phe Tyr Ala
1               5

<210> SEQ ID NO 37
<211> LENGTH: 9
<212> TYPE: PRT
<213> ORGANISM: Artificial Sequence
<220> FEATURE:
<223> OTHER INFORMATION: Synthetic polypeptide (CMV NV9)

<400> SEQUENCE: 37

Asn Leu Val Pro Met Val Ala Thr Val
1               5

<210> SEQ ID NO 38
<211> LENGTH: 10
<212> TYPE: PRT
<213> ORGANISM: Artificial Sequence
<220> FEATURE:
<223> OTHER INFORMATION: Synthetic polypeptide (MART-1)

<400> SEQUENCE: 38

Glu Leu Ala Gly Ile Gly Ile Leu Thr Val
1               5                   10

<210> SEQ ID NO 39
<211> LENGTH: 10
<212> TYPE: PRT
<213> ORGANISM: Artificial Sequence
<220> FEATURE:
<223> OTHER INFORMATION: Synthetic polypeptide (MART-1 Refolded)

<400> SEQUENCE: 39

Glu Leu Ala Gly Ile Gly Ile Leu Thr Val
1               5                   10

<210> SEQ ID NO 40
<211> LENGTH: 8
<212> TYPE: PRT
<213> ORGANISM: Artificial Sequence
<220> FEATURE:
<223> OTHER INFORMATION: Synthetic polypeptide (gTAX Refolded)

<400> SEQUENCE: 40

Leu Phe Gly Tyr Pro Val Tyr Val
1               5

<210> SEQ ID NO 41
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 41

Tyr Pro Asn Val Asn Ile His Asn Phe
1               5

<210> SEQ ID NO 42
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 42

Gln Leu Ser Pro Phe Pro Phe Asp Leu
1               5

<210> SEQ ID NO 43
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 43

Tyr Pro Leu Thr Phe Gly Trp Cys Phe
1               5

<210> SEQ ID NO 44
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 44

Ala Ile Ala Asp Ile Ser Tyr Ser Val
1               5

<210> SEQ ID NO 45
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 45

Ser Leu Leu Asp Asp Ala Phe Ala Leu
1               5

<210> SEQ ID NO 46
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 46

Arg Val Ala Asp Tyr Ile Val Lys Val
1               5